United States Patent [19]

Hilvert et al.

[11] Patent Number: 5,208,152
[45] Date of Patent: May 4, 1993

[54] CATALYSTS OF DIELS-ALDER REACTIONS, METHODS AND CATALYSTS THEREFOR

[75] Inventors: Donald Hilvert; Kenneth W. Hill, both of San Diego, Calif.

[73] Assignee: The Scripps Research Institute, La Jolla, Calif.

[21] Appl. No.: 842,792

[22] Filed: Feb. 27, 1992

Related U.S. Application Data

[63] Continuation of Ser. No. 422,643, Oct. 17, 1989, abandoned.

[51] Int. Cl.$^5$ .................. C12P 17/18; C12N 9/00
[52] U.S. Cl. .................. 435/119; 435/188.5
[58] Field of Search ........... 435/119, 121, 183, 188.5, 435/280; 530/388.9

[56] References Cited

U.S. PATENT DOCUMENTS 4,888,281 12/1989 Schochetman et al. ........... 435/72

OTHER PUBLICATIONS

Raasch, M. S. (1980) J. Org. Chem. 45, 867–870.
Hilvert, D. et al. (1988) Proc. Nat. Acad. Sci., U.S.A. 85, 4953–4955.
Organic Chemistry (Allinger, et al., eds.) Worth Pub. Inc., 1971, pp. 130–133.
Boger, Chem. Rev., 86:781–793 (1986).
Jacobi et al., J. Org. Chem. 46:2065–2069.
Corey et al., J. Am. Chem. Soc., 95:2303–2311 (1973).
Grant & Hackh's Chemical Dictionary, p. 248 (1987).
Official Gazette, p. 232 Jun. 7, 1983.
Jacobs, Biotechnology, 9:258–262, 259 (Mar. 1991).
Hilvert et al., J. Am. Chem. Soc., 111:9261–9262 (1989).
Anon., C&EN, p. 17, Jan. 1, 1990.

Primary Examiner—Charles L. Patterson, Jr.
Attorney, Agent, or Firm—Dressler, Goldsmith, Shore, Sutker & Milnamow, Ltd.

[57] ABSTRACT

Molecules that catalyze the reaction of a cyclic conjugated diene having a fugitive leaving group in a five- or six-membered ring containing the conjugated double bonds and a dienophile that contains a reactive multiple bond to form a reaction product that contains a five- or six-membered ring and at least two endocyclic double bonds from a Diels-Alder [4+2] cycloaddition/fragmentation reaction that is followed by a reverse Diels-Alder reaction are disclosed. The catalyst molecules contain an antibody combining site that immunoreacts with an antigen whose structure (i) includes a [2.2.1] or [2.2.2] bicyclic ring system that is absent from the reaction product and (ii) contains at least one endocyclic double bond fewer than the number of endocyclic double bonds present in the reaction product. Methods of preparing and using the catalyst molecules are also disclosed.

29 Claims, 1 Drawing Sheet

2 R= $(CH_2)_5COOH$
3 R= Et

CATALYSTS OF DIELS-ALDER REACTIONS, METHODS AND CATALYSTS THEREFOR

This application is a continuation of application Ser. No. 07,422,643, filed Oct. 17, 1989.

DESCRIPTION

1. Technical Field

The present invention relates to Diels-Alder [4+2] cycloaddition reactions, and more particularly to the catalysis of such reactions by molecules that contain an antibody combining site.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding may lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively, by a lipase.

Slobin, *Biochemistry*, 5:2836–2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies was said to inhibit the hydrolysis of the aminocaproate ester.

Kohen and co-workers also reported attempts using antibodies to catalyze esterolysis. The antibodies utilized by this group were, in each instance, raised to a portion of the ultimately utilized substrate molecule that did not contain the bond to be hydrolyzed.

In their initial work [*FEBS Letters*, 100:137-140 (1979) and *Biochim. Biophys. Acta*, 629:328-337 (1980)] anti-steroid antibodies were used to hydrolyze 7-umbelliferone (7-hydroxycoumarin) esters of a carboxyethyl thioether of a steroid. In each instance, an increase in hydrolytic rate was observed as compared to background or to a rate obtained with normal IgG. In both instances, turnover numbers were low (about one mole of substrate per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolyses of 7-[-N-(2,4-dinitrophenyl)-6-aminohexanoyl]-coumarin using monoclonal antibodies raised to the dinitrophenyl portions of that substrate molecule [*FEBS Letters*, 111:427-431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex will impede catalysis. Such is thought to be the situation for the results reported by Kohen and co-workers.

The above constructs, though interesting, are severely limited by the failure to address the mechanism of binding energy utilization which is essential to enzymes [W. P. Jencks, *Adv. Enzymol.*, 43, 219 (1975)].

Those deficiencies can be redressed by using a transition state analog as the immunizing hapten to elicit the desired antibodies. This hapten can assume the role of an inhibitor in the catalytic system.

Thus, immunological binding can be used to divert binding interactions to catalytic processes. For example, it was suggested that use of an antibody to a haptenic group that resembles the transition state of a given reaction should cause an acceleration in substrate reaction by forcing substrates to resemble the transition state. Jencks, W.P., *Catalysis in Chemistry and Enzymology.* page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions cannot be isolated, as compared to intermediates, which are generally isolable. Although the above hydrolytic transition states cannot be isolated, a large amount of scientific literature has been devoted to the subject.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity; i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolytic proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

For example, modern genetic engineering techniques have been useful in preparing fusion proteins that contain a desired protein or polypeptide fused to the transcription product of a vector gene such as the lac z gene. The use of such fusion proteins is, however, hindered by the presence of fragments of the vector gene product. It would also therefore be beneficial if proteolytic enzyme-like molecules could be developed that would cleave such fusion products between the wanted and unwanted fusion polypeptide or protein portions.

Recently, Lerner, Tramontano and Janda [*Science*, 234, 1566 (1986)] reported monoclonal antibodies that catalytically hydrolyzed an ester. Tramontano and Lerner also describe using monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analog of the tetrahedral hydrolytic transition state of the carboxylic acid ester or carbonate ester. The Pollack et al. antibody principally discussed was a myeloma protein that happened to bind to a phosphonate that was structurally analogous to the carbonate analog hydrolyzed. Thus, in the Lerner and Tramontano et al. work, the substrate to be hydrolyzed was preselected, with the immunizing analog and hydrolytic antibodies being synthesized in accordance with the desired product. Pollack et al. designed the substrate to be hydrolyzed once they knew the specificity of the myeloma protein. Pollack et al. also reported (above) the existence of a catalytic antibody, substrate and transition state analog system for carbonate hydrolysis similar in concept to that of Lerner et al. Work relating to that system is reported in Jacobs et al., *J. Am. Chem. Soc.*, 109, 2174 (1987).

Published patent application WO 85/02414 discusses the possible use of antibodies as catalysts, and presents data relating to the use of polyclonal serum in hydrolyzing o-nitrophenyl-beta-D-galactoside. The antibodies useful in that application are said to be inducible by a reactant, a reaction intermediate or to an analog of the reactant, product or reaction intermediate. The term "analog" is there defined to encompass isomers, homologs or other compounds sufficiently resembling the reactant in terms of chemical structure that an antibody raised to an analog can participate in an immunological reaction with the reactant but will not necessarily catalyze a reaction of the analog.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turn over of the allegedly catalytic antibody was shown, nor was there an indication of the percentage of substrate galactoside cleaved. That application did indicate that beta-D-galactosidase cleaved about ten times as much substrate as did the polyclonal antibodies, presuming linearity of absorbance at the unnamed concentration of substrate studied.

From the data presented in that application, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

More recently, antibodies that promote photochemical processes [Bolan et al., *J. Chem. Soc., Chem. Commun.*, 106 (1988)], a sigmatropic rearrangement [Hilvert et al., *Proc. Natl. Acad. Sci. USA*, 85:4953 (1988); Jackson et al., *J. Am. Chem. Soc.*, 110:4841 (1988)], and a $\beta$-elimination [Shokat et al., *Nature* (London), 338:269 (1989)] have been reported. A catalyzed hydrolysis by antibodies in a reverse micelle system was also recently reported [Dufor et al., *J. Am. Chem. Soc.*, 110:8713-8714 (1988)].

The Diels-Alder reaction is the prototype of a broad and important class of pericyclic processes. It involves the concerted addition of an unsaturated molecule (dienophile; e.g., an olefin or another doubly or triply bonded species) across the 1,4-positions of a conjugated diene. A Diels-Alder reaction is an example of a [4+2] cycloaddition reaction. The Diels-Alder reaction is not usually subject to chemical catalysis by nucleophiles, general acids or general bases, but the reaction rate is enhanced when carried out in water, under pressure, or in the presence of Lewis acids or cyclodextrins.

Although no Diels-Alderases are known in nature, the Diels-Alder reaction should be subject to enzymatic catalysis, especially proximity effects. The equilibrium and activation entropies for a typical bimolecular Diels-Alder reaction are found to be in the range of $-30$ to $-40$ cal $K^{-1}$ mol$^{-1}$, primarily due to the loss of translational and rotational entropy [Sauer, *Angew. Chem., Int. Ed. Engl.*, 6:16 (1967); Wasserman, *Diels-Alder Reactions*, Elsevier Publ. Co., Amsterdam (1965)]. This substantial entropy loss could be avoided if the reactants were bound to an antibody. If the losses of translational and rotational degrees of freedom are paid for in the binding step, rate enhancements as high as $10^8$ M in rate (for 1 M standard states) could conceivably be achieved in an antibody-mediated process.

Since naturally-occurring Diels-Alderases have never been found, transition state analogs of the [4+2] cycloaddition reaction have not been previously developed. However, the transition state of the bimolecular Diels-Alder reaction is highly ordered, resembling the product more closely than the starting materials. Although the product itself could be used as an immunizing hapten (immunogen), any antibodies elicited would bind that material most tightly. Severe product inhibition would therefore limit the practicality of any antibodies produced that accelerated the rate of the Diels-Alder reaction.

It would therefore be beneficial if a more specific catalyst for a Diels-Alder [4+2] cycloaddition reaction could be found, and if such a catalyst would not suffer substantially from product inhibition. The disclosure that follows illustrates such a catalyst.

BRIEF SUMMARY OF THE INVENTION

The present invention contemplates catalyst molecules, and their methods of preparation and use in Diels-Alder [4+2] cycloaddition/fragmentation reactions.

A catalyst molecule of the invention comprises an antibody combining site-containing molecule that is preferably monoclonal and catalyzes the formation of a cyclic reaction product. That cyclic reaction product is formed from a reactant dienophile molecule that contains a reactive multiple bond and a reactant conjugated cyclic diene molecule that has a structure that includes a fugitive leaving group within a five- or six-membered ring. The reaction product has a newly formed ring that contains five or six atoms (a five- or six-membered ring) and at least two conjugated endocyclic double bonds. The catalyst not only catalyzes the reaction but also immunoreacts with an antigen whose structure (i) includes a [2.2.1] or [2.2.2] bicyclic ring structure that is absent from the reaction product and (ii) contains one endocyclic double bond fewer in that bicyclic ring system than the number of endocyclic double bonds present in the reaction product.

In preferred practice, the catalyst molecule is an intact antibody, the reactant dienophile molecule has a cyclic structure, and the fugitive leaving group forms a gaseous compound (at atmospheric pressure) upon formation of the reaction product. The reactant diene and dienophile molecules are also preferably substituted with one or more substituent groups other than hydrogen, as is the reaction product substituted with the same or substantially corresponding groups.

Where a preselected structural isomer of a cyclic reaction product is desired to be formed in an increased proportion relative to another structural isomer that could be formed in an uncatalyzed reaction, the catalyst also binds to (immunoreacts with) an antigen whose structure contains a substituent that corresponds substantially to an asymmetrically substituted substituent present in at least one of the reactant diene and dienophile molecules, and that is present at an analogous location in the preselected cyclic reaction product. For formation of a preselected stereoisomer in an increased proportion relative to another stereoisomer such as an enantiomer or a diastereomer, the catalyst molecule also immunoreacts with an antigen that contains one or more substituents that correspond substantially to a substituent or substituents present in the reactants, and which substituent or substituents are present at an analogous location and stereoconfiguration in the preselected stereoisomeric cyclic reaction product.

A cyclic reaction product that includes at least two endocyclic conjugated double bonds in a five- or six-membered ring is produced in a method embodiment of the present invention. Here, a reactant dienophile molecule having a reactive multiple bond and a reactant cyclic conjugated diene molecule having a structure that includes a fugitive leaving group within a five- or six-membered ring are admixed with a catalyst molecule (present in a catalytically effective amount) in a liquid composition to form a reaction mixture. The catalyst molecule is a monoclonal antibody combining site-containing molecule that catalyzes the reaction and is as described before. The reaction mixture is maintained for a time period sufficient for the cyclic reaction product to form.

Preferences for the catalyst molecule are as discussed previously. Where the cyclic reaction product is a derivative of cyclohexadiene, a further step of oxidizing that material to a corresponding benzene derivative is often preferred. The liquid composition utilized is often an aqueous composition that can contain up to about 20 percent by volume of an organic solvent, although substantially anhydrous organic solvents and reverse micelle compositions are also contemplated.

In another aspect of the above method embodiment, the proportion of a preselected cyclic reaction product structural isomer formed in a reaction that forms a plurality of structural isomeric cyclic reaction products is enhanced relative to the proportion of the other structural isomer(s) that could form in an uncatalyzed reaction. The method steps here are similar to those discussed above, but at least one of the reactant conjugated diene and reactant dienophile molecules is asymmetrically substituted. In addition, as noted before, the structure of the antigen bound by the catalyst molecule contains a substituent that corresponds substantially to the asymmetrically substituted substituent present in at least one of the reactant conjugated diene or reactant dienophile molecules, and is present at an analogous position or location in the preselected cyclic stereoisomeric reaction product.

A further aspect of this method embodiment is a catalytic method for increasing the proportion of a preselected cyclic reaction product stereoisomer formed in a reaction that forms stereoisomeric cyclic reaction products in an uncatalyzed reaction. The method steps here are again similar to the steps of the above-described methods, except that the reactant cyclic conjugated diene and dienophile molecules include one or more substituent groups that give rise to possible stereoisomeric cyclic reaction products. Exemplary of such substituent groups are chiral centers on one or more substituents. In another example, a chiral center is formed in a reaction product cyclohexadiene derivative where the dienophile molecule itself contains a reactive double bond that includes one carbon atom that is asymmetrically substituted; i.e., contains two different substituents. The structure of the antigen to which the catalyst molecule binds (or with which it immunoreacts) here includes a [2.2.1] or [2.2.2] bicyclic ring system and contains one fewer endocyclic double bonds than the cyclic reaction product as noted previously, and also contains one or more substituents that correspond substantially to the substituent or substituents present in the reactant molecules, and which substituent or substituents are present at an analogous location and stereoconfiguration in the preselected stereoisometric cyclic reaction product, as was noted earlier.

The preselected stereoisomer can be a single enantiomer or diastereomer, or an enantiomeric pair of diastereomers.

The reactant conjugated diene molecule and reactant dienophile molecule discussed previously are typically each substituted with one or more substituent groups other than hydrogen. The cyclic reaction products produced by the various aspects of the method embodiment of the invention can also be isolated or otherwise recovered.

A method of preparing a before-described monoclonal antibody combining site-containing catalyst molecule is another embodiment of this invention. Here, a mammalian animal host such as a mouse, rabbit or goat is immunized with a relatively non-reactive immunogen having a structure that is isologous to the structure of a Diels-Alder [4+2] cycloaddition product formed by the reaction of a dienophile molecule containing a reactive multiple bond and a cyclic conjugated diene molecule that also includes a fugitive leaving group in a five- or six-membered ring and that is a reactive intermediate in the formation of the cyclic reaction product. The structure of the immunogen includes a [2.2.1] or [2.2.2] bicyclic ring system that is absent from the cyclic reaction product, and at least one endocyclic double bond per molecule in that ring bicyclic system fewer than the number of endocyclic double bonds present in the reaction product.

Hybridoma cells are formed from antibody-secreting cells of the immunized mammalian animal host that secretes antibodies that immunoreact with the immunogen. The hybridoma cells that secrete antibodies that immunoreact with the immunogen are then cloned and cultured to secrete the monoclonal antibody catalyst molecules.

Where monoclonal catalyst molecules are desired that catalyze formation of preselected structural or stereoisomers, the immunogen structure includes appropriately located substituent groups, and those groups are in an appropriate stereoconfiguration, where a stereoisomeric cyclic reaction product is desired.

Reactive amino acid side groups and/or the amino-terminal amino groups of the catalyst molecules can also be reacted with protective groups that do not substantially inhibit the reaction catalyzed. Amino groups can illustratively be reductively alkylated using formaldehyde and sodium cyanoborohydride.

BRIEF DESCRIPTION OF THE DRAWING

In the drawing that forms a portion of this disclosure.

DETAILED DESCRIPTION OF THE INVENTION

I. Introduction

Figure 1:
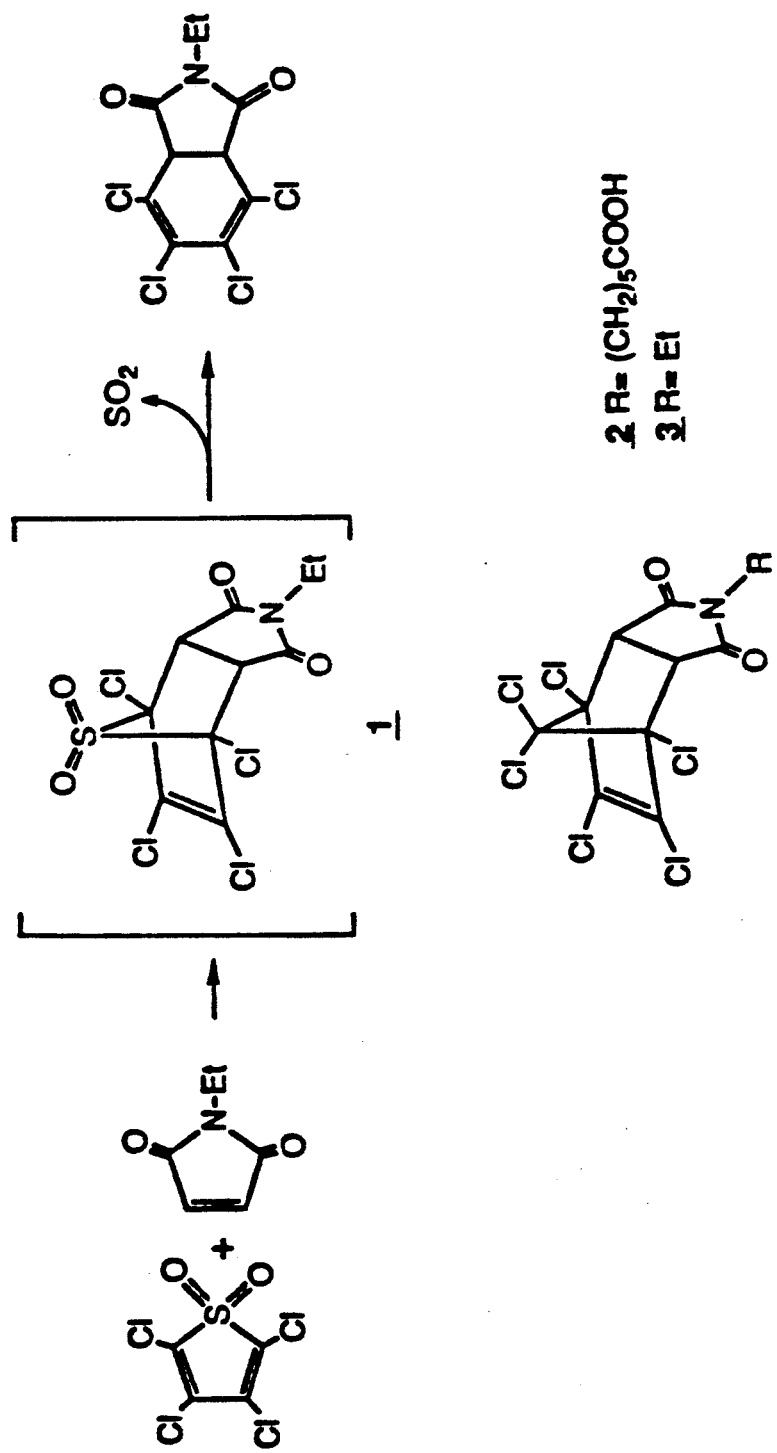
FIG. 1 is a schematic depiction of the uncatalyzed reaction of tetrachlorothiophene dioxide (TCTD) with N-ethyl maleimide to form the reactive, bicyclic, intermediate Compound 1, that subsequently extrudes $SO_2$ gas (arrow) to form N-ethyl dihydrophthalimide as the reaction product. Compound 2, shown below Compound 1 [R=$(CH_2)_5COOH$], is a Diels-Alder [4+2] cycloaddition product isologous to Compound 1, that was linked to an immunogenic carrier (keyhole limpet hemocyanin) and used as a haptenic immunogen to induce the monoclonal antibodies that catalyze the reaction shown in the scheme. Compound 3 [R=Et, ethyl], was used as a competitive inhibitor antigen for the catalytic reaction.

The present invention relates to Diels-Alder [4+2] cycloaddition/fragmentation reactions that are catalyzed by a catalyst molecule containing an antibody combining site. The catalysis exerted by the catalyst molecule can be manifest in the rate of a given reaction, as well as in the stereoselectivity and regioselectivity of the reaction catalyzed. Thus, as is the case with many enzymes, a catalyst described herein can speed the progress of a chosen reaction, and can also enhance the relative proportion of a preselected reaction product that is formed. A catalyst molecule that enhances the rate at which the starting diene and dienophile molecules are consumed need not, however, also enhance stereo- or regioselectivity of the formation of a desired reaction product, and vice versa.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze the hydrolysis of proteins by combining with the protein to stabilize the transition state of the hydrolysis reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W.P., *Adv. Enzymology*, 43, 219 (1975) and Pauling, L., *Amer. Scientist*, 36, 58 (1948)].

Support for this theory comes from the observation that substances that are thought to model the presumed transition states are often strongly bound to the enzymes as competitive inhibitors. Leinhard, G., *Science*, 180, 149 (1973) and Wolfenden, R., *Acc. Chem. Res.*, 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W.P., *XVII International Solvav Conference* (November 1983)].

The converse proposition is that a paratope-containing (antibody combining site-containing) molecule that is prepared to optimally bind a suitable analog of a transition state would function as a catalyst. The demonstration of this result completes the correlation of enzyme function and antibody structure and provides a useful approach to devising artificial enzymes except where the transition state so resembles the product formed that binding of that product inhibits the reaction to be catalyzed.

The chemistry of the present invention is straightforward and well known to those skilled in synthetic organic chemistry. See, for example, D.L. Boger and S.N. Weinreb, *Hetero Diels-Alder Methodology in Organic*

*Synthesis,* Academic Press, San Diego, Calif. (1989). That chemistry involves a Diels-Alder [4+2] cycloaddition reaction to form a bicyclic reactive intermediate containing a fugitive leaving group that is followed by a fragmentation reaction to form the cyclic reaction product that contains one double bond more than the reactive intermediate.

The reaction specifically illustrated herein can be termed a "simple" fragmentation, inasmuch as further reactions are not required to cause expulsion of the fugitive leaving group. However, reactions of a reactive intermediate in addition to "simple" fragmentation reactions are also contemplated herein. For example, reaction of an oxazole with an appropriate dienophile can lead to formation of a bicyclic reactive intermediate that contains a bridging ether oxygen atom. Subsequent protonation of the ether oxygen atom that can be catalyzed by amino acid residue side groups of the antibody combining site catalyst molecule or by species present in an uncatalyzed reaction mixture can result in fragmentation of the intermediate to expel water. A dihydropyridine (a cyclic conjugated diene) reaction product is thereby formed that can be oxidized or eliminate appropriate substituents to form a pyridine derivative. Boger, *Chem. Rev.*, 86:781-793 (1986).

Fragmentation reactions that require protonation or other reactions are considered "complex" fragmentations herein to distinguish such reactions from "simple" fragmentation reactions in which all of the atoms of the fugitive leaving group are present in the reactive intermediate and no further reactions are required for expulsion of the fugitive leaving group. "Simple" fragmentation reactions are thus akin to reverse Diels-Alder reactions. Indeed, the expulsion of CO from a substituted bicycle 2.2.1] heptenone and $CO_2$ from a substituted unsaturated bicyclic lactone are classed as reverse Diels-Alder reactions, J. March, *Advanced Organic Chemistry,* 3rd ed., John Wiley & Sons, New York, page 930 (1985).

Both types of fragmentation reactions are collectively referred to herein as fragmentation reactions, unless one or the other type of fragmentation is specifically recited. The overall reaction is therefore referred to as a Diels-Alder [4+2] cycloaddition/fragmentation reaction.

For ease of expression and understanding, the ultimately formed compound (the compound formed after the fragmentation reaction) is generally referred to herein as the "cyclic reaction product" or "reaction product", whereas the first-formed Diels-Alder product is referred to as the "reactive intermediate" or "intermediate" even though it is itself a reaction product.

The basic idea behind the immunological catalysis described herein contemplates the use of an immunizing hapten (immunogen) that resembles the reactive intermediate in structure; i.e., is isologous to the reactive intermediate, to induce production of molecules that contain an antibody combining site (paratope) to the hapten as an antigen. The immunizing haptenic molecule is stable relative to the reactive intermediate under the conditions of its own synthesis and use as an immunogen or antigen, but need not be completely inert to any possible chemical reactions that it might encounter.

The transition state for the formation of a Diels-Alder [4+2] cycloaddition product resembles the product of that reaction, the reactive intermediate, but is thought to have slightly longer bond lengths. Thus, in preferred practice, the isologous hapten is slightly larger than the corresponding reactive intermediate whose size and shape it mimics. In addition, if only the first reaction that forms the reactive intermediate were contemplated, that reaction product would bind to the catalyst molecule and inhibit further reactions.

The induced antibody catalyst molecules can stabilize the transition state for the formation of the reactive intermediate. However, the reactive intermediate that is formed is generally, so reactive, e.g., at ambient room temperature, that it is not recoverable.

Rather, that reactive intermediate undergoes a second reaction, a fragmentation reaction, in which the fugitive leaving group is expelled or extruded, usually as a gas, to form a reaction product that itself can be recovered, or that can form a recoverable reaction product after a subsequent reaction. Once the fugitive leaving group is expelled, the reaction product formed is sufficiently different in size and shape from the reactive intermediate that the reaction product does not cause substantial product inhibition by binding to the catalyst molecule, and the catalyst molecule can catalyze further reactions, or "turnover". In addition, expulsion of the fugitive leaving group drives the reaction forward, and substantially eliminates the possibility of a reverse Diels-Alder [4+2] cycloaddition reaction occurring to form the original reactants.

It is noted that the decomposition of the reactive intermediate need not be, but preferably is, faster than is the formation of that material. Thus, the rate of decomposition can also be equal to or slower than is the rate of formation.

Thus, a catalyst molecule of the present invention binds to the reacting diene and dienophile molecules, stabilizes the transition state for the Diels-Alder [4+2] cycloaddition reaction between those reactants, and exhibits a binding preference for the formed reactive intermediate and isologous haptenic antigen (immunogen) over the reaction product so that the catalyst turns over.

The catalyst molecules used herein thus are induced by and bind to a molecule having a different structure than either the starting reactants or the reaction product, although the same or substantially corresponding substituent groups are present in the reactants and immunizing hapten. This concept of catalyst molecule formation is therefore different from that of Lerner et al. discussed previously where the immunogen structure is analogous to that of the hydrolytic transition state leading directly to the isolated product.

This concept is also different from the broad concepts disclosed in WO 85/02414 in which the reactant or product could be used as immunogen, as could an analog of the product, reactant or reaction intermediate. The present catalyst molecules thus avoid the problem of production inhibition that is inherent in the catalyst disclosed in WO 85/02414.

The mechanism by which a paratope-containing molecule catalyzes the formation of the reaction product from bound reactants can be thought of in terms of an "induced fit" model. As the loosely bound reactant molecules distort or rearrange to conform to the binding geometry of the antibody combining site, stress can be relieved by chemical reorganization of predetermined unsaturated bonds such that this reorganization leads to the formation of new bonds and reorganization of others.

The terms "antibody combining site-containing molecule", "paratope-containing molecule" and "catalyst molecule" are used interchangeably herein to mean a biologically active molecule that binds to reactants and catalyzes the before-described reaction. An "antibody combining site" or "paratope" is that structural portion of an antibody molecule comprised of heavy and light chain variable and hypervariable regions that specifically binds antigen. The catalyst molecules of the present invention are antibodies, substantially intact antibodies, idiotype-containing polyamide portions of an antibody or recombinant antibody combining site portions as are discussed hereinafter.

Biological activity of a catalyst molecule is evidenced by the binding of the catalyst to its immunogenic hapten or inhibitor hapten as antigenic ligands upon their admixture in an aqueous composition, at least at physiological pH values and ionic strengths. The catalyst molecule can therefore be viewed as a receptor. Preferably, the receptor catalyst molecules also bind to an antigenic ligand (the hapten) within a pH value range of about 5 to about 9, and at ionic strengths such as that of distilled water to that of about one molar sodium chloride. Temperatures ranging from the freezing point of the aqueous composition (about zero degree C.) to the boiling point of such a composition (about 100 degrees C.) can be used, although temperatures of about 15 degrees C. to about 40 degrees C. are preferred. These ionic strength, pH and temperature conditions utilized at atmospheric pressure are referred to herein as "biological conditions".

Paratopes or antibody combining site portions of antibodies are those portions of antibody molecules that include the idiotype or paratope, and bind to the ligand. Such portions include the Fab, Fab' and F(ab')$_2$ fragments prepared from antibodies by well-known enzymatic cleavage techniques. See for example, U.S. Pat. No. 4,342,566 to Theofilopoulos and Dixon, generally, and specifically, Janda et al., *Science.* 241:1188-1191 (1988) and pollack et al. *Science,* 234, 1570 (1987) who reported accelerated hydrolytic rates for Fab fragments were about the same as those of the native Ig. F(v) antibody portions are generally prepared by recombinant techniques as can other antibody combining site-containing portions.

Inasmuch as the antibodies from which paratope-containing portions are obtained are described as raised against or induced by immunogens, paratope-containing portions are discussed as being "raised" or "induced" with the understanding that a cleavage step is typically required to obtain a paratope-containing portion from an antibody. Intact antibodies are preferred, however, and are utilized as illustrative of the catalyst molecules of this invention.

The words "immunogen" and "antigen" in their various grammatical forms were historically used interchangeably. More recently, however, the word "immunogen" has been utilized to mean the entity that induces production of antibodies, whereas the word "antigen" is used to mean the entity that is specifically bound by (immunoreacts with) the induced antibodies. This change in usage reflects the fact that antibody combining sites can immunoreact with molecules other than those that induced them. The words "immunogen" and "antigen" and their various grammatical forms are utilized herein in their more recent meanings even though the same entity is utilized for inducing and immunoreacting with antibodies, or both words are utilized together.

The term "antibody" in its various grammatical forms is used herein to refer to a composition containing a plurality of antibody molecules, e.g., an antiserum. An antibody containing intact antibody molecules is preferred. Particularly preferred is a monoclonal antibody.

The catalyst molecules useful in the present invention are preferably monoclonal antibodies or paratope-containing portions thereof. The phrase "monoclonal antibody" in its various grammatical forms refers to an antibody containing only one species of antibody combining site capable of immunoreacting with a particular antigen and thus typically displays a single binding affinity for that antigen. A preferred monoclonal antibody catalyst is characterized as containing, within immunologically detectable limits, only one species of antibody combining site capable of immunologically binding (immunoreacting with) an antigenic hapten described herein and catalyzing the Diels-Alder [4+2] reaction described herein.

A "monoclonal antibody" is secreted by clones of a single cell called a hybridoma that secretes but one kind of catalyst molecule. The hybridoma cell results from fusing an antibody-producing cell and a myeloma cell or other self-perpetuating cell line.

Techniques for preparing the monoclonal antibodies of the present invention are well known. Such receptors were first described by Kohler and Milstein, *Nature,* 256, 495 (1975), which is incorporated herein by reference. The preparation of monoclonal antibodies and their subsequent purification sufficient for use in the present invention are well known. Typically, a monoclonal antibody is prepared from a hybridoma culture supernatant by separating the supernatant from cultured hybridoma cells to form a cell-free monoclonal antibody molecule-containing solution. Alternatively, a monoclonal antibody can be prepared from ascites by introducing a hybridoma cell, as by injection, into the peritoneal cavity of a mammal such as a mouse and later harvesting the resulting peritoneal exudate (ascites tumor fluid) from the mouse by well known techniques. See, for example, H. Zola, *Monoclonal Antibodies: A Manual of Techniques,* CRC Press, Inc. (1987).

Additionally, a monoclonal antibody can be produced by recombinant DNA methodologies in which a monoclonal antibody molecule-encoding gene is cloned and manipulated into a suitable expression medium for production of a recombinantly produced antibody molecule, or for the expression of the paratope-containing portion thereof. Such molecules are referred to herein as a "recombinant monoclonal antibody" "recombinant antibody combining site-containing molecule". These techniques are discussed below.

The preparation of recombinant monoclonal antibodies of the present invention can be accomplished using well known methods that involve the cloning of immunoglobulin genes, the subsequent manipulation of the cloned genes and their introduction into a suitable expression vector and expression medium, and the production of the resulting hybrid protein molecules to form recombinant monoclonal antibodies or paratope-containing portions thereof. The above-recited preparative steps are routine recombinant DNA cloning, manipulation and expression procedures, and are described in more detail hereinbelow. The inventive aspect of a recombinant monoclonal antibody does not reside in the techniques for preparing a monoclonal antibody, but rather in the resulting manipulated gene, and the gene's expressed antibody molecule having an antibody combining site that immunoreacts with an antigen and catalyzes a reaction as described herein.

The cloning of immunoglobulin protein-encoding genes, and their manipulation to form recombined DNA molecules that encode antibody combining sites are generally known methods. Once prepared, these recombined DNA molecules are introduced into an expression medium that produces assembled antibody containing site-containing molecules that are capable of immunoreaction with the same specificity as the antibody produced by the antibody secreting cell from which the immunoglobulin protein-encoding genes were isolated. See, for example Roberts et al., *Protein Engineering*, 1:59-65 (1986), Morrison, *Science*, 229:1202-07 (1985), U.S. Pat. No. 4,474,893, and published patent application Nos. EP 0125023, EP 0239400 and WO 89/00999.

For the isolation of an immunoglobulin protein-encoding gene in preparation of a monoclonal antibody, the gene can be obtained from any cell that produces an antibody molecule that immunoreacts with a desired antigenic hapten. A preferred cell is a hybridoma cell. Hybridomas can be prepared as disclosed herein.

The immunoglobulin protein-encoding genes of a lymphoid cell, such as a hybridoma, can be isolated by either cloning genomic DNA fragments containing the paratope-containing immunoglobulin genes, or by cloning antibody-specific mRNA molecules in the form of complementary DNA (cDNA) fragments, as is well known. The identification of the immunoglobulin encoding gene fragments, once cloned, is achieved typically by screening the obtained clones with polynucleotide probes in a hybridization assay. The probes are complementary in nucleic acid sequence to portions of the immunoglobulin genes that encode the monoclonal antibody heavy and light chain subunits comprising an immunoglobulin protein molecule that includes the paratope.

Polynucleotide probe preparation and the use of such probes in hybridization screening of cloned gene libraries is well known. The choice of the probe's nucleic acid sequence is typically determined by amino acid sequencing of at least portions of isolated immunoglobulin protein subunits. In addition sequences that are conserved for several mammalian species are reported in Kabat et al., *Sequences of Proteins of Immunological Interest*, National Institutes of Health, Bethesda, Md. (1987).

In yet another embodiment, single-chain antigen-binding proteins are utilized. Such proteins include the $V_L$ and $V_H$ portions of a useful antibody molecule linked together in a single chain, rather than as two separate chains. Single-chain antigen-binding proteins are also prepared by recombinant DNA techniques and are therefore included among the recombinant paratope-containing molecules. Such molecules are prepared as described in Bird et al., *Science*, 242:423-426 (1988) and U.S. Pat. No. 4,704,692, whose disclosures are incorporated by reference.

Numerous variations on the above cloning, preparation of expression vectors and final expression and harvesting of immunoglobulin proteins are readily apparent to one skilled in the art.

For examples of general recombinant DNA cloning methods, see *Molecular Cloning*, Maniatis et al., Cold Spring Harbor Lab., N.Y., (1982); *DNA Cloning*, Glover, ed., IRL Press, McLean, Va. (1985)). For the genomic cloning and expression of immunoglobulin genes in lymphoid cells, see Neuberger et al., *Nature*, 312:604-8 (1984); Ochi et al., *Proc. Natl. Acad. Sci. USA*. 80:6351-55 (1987); and Oi et al., *Proc. Natl. Acad. Sci. USA*, 80:825-29 (1983). For cloning of immunoglobulin genes from hybridoma cells, and their expression in *Xenoous* oocytes, see Roberts et al., *Protein Engineering*, 1:59-65 (1986), and see Wood et al., *Nature*, 314:446-9 (1985) for their expression in yeast.

From the above it is seen that a paratopic portion of a monoclonal antibody molecule of this invention can be produced by various means that include the use of cloned immunoglobulin-encoding genes. Therefore, it is to be understood that once a particular monoclonal antibody is prepared by the conventional immunization and cell-fusion methods to yield the original antibody-producing hybridoma cell, that same antibody can subsequently be produced by numerous recombinant DNA methodologies.

Thus, the present invention contemplates a monoclonal antibody composed of an assemblage of heavy (H) and light (L) chain protein subunits arranged as an immunoglobulin molecule having the formula $H_2L_2$ whose amino acid sequences each correspond through the genetic code to the nucleotide sequence of mRNA molecules present in a hybridoma capable of producing a catalytic antibody molecule as described herein.

Monoclonal antibody catalysts are preferably utilized herein because of their unique specificity in binding to a particular epitope such as a particular immunizing hapten as antigen, as well as their relatively higher specific catalytic activity as compared to polyclonal antibodies. Polyclonal antibody preparations can also be used herein, but typically have to be separated into fractions that bind to the immunizing or an antigenic hapten and those that bind to extraneous epitopes such as those of the immunogenic carrier.

Polyclonal antibodies that bind to an appropriate hapten can be separated by affinity separation using the immunogenic hapten as the antigen of an affinity sorbent. After admixture and maintenance of an antibody preparation with the affinity sorbent for a time sufficient for appropriate immunoreaction (binding) to take place, the affinity sorbent is separated from the remaining portion of the antibody preparation.

The separated, remaining antibody portion bound to the affinity sorbent contains the antibodies that bind to the hapten, whereas antibodies in the separated remaining portion of the antibody preparation bind to extraneous epitopes. Those affinity-bound antibodies can thereafter be isolated by usual techniques for separating bound entities from affinity sorbents, such as washing the sorbent with glycine-hydrochloride at pH 2.

A ligand is defined herein as a molecule or molecules that immunoreacts with or binds to a catalyst molecule antibody combining site. Two types of ligand are contemplated herein. A first is termed an immunogenic (antigenic) ligand and is used as an immunogen to induce preparation of catalyst molecules, and as an inhibitor (antigen) of the catalyzed reaction, in an affinity sorbent as discussed before, or to screen potential catalyst molecules for their ability to immunoreact. The second is referred to as the ligand, reactant ligand, reactant ligand substrate or simply the reactant or reactants and is the two molecules or two portions of a single molecule (diene and dienophile) that undergo the catalyzed reaction. The immunogenic and antigenic ligands (haptens) are substantially inert to undergoing the catalyzed reaction, as already noted.

II. Diels-Alder Transition State and Hapten Design

Design of the immunizing, relatively non-reactive hapten that is isologous to a Diels-Alder [4+2] cycloaddition reactive intermediate flows backward from the structure of the reaction product to be formed, through the Diels-Alder [4+2] cycloaddition reactive intermediate, to the transition state for bond formation of that reactive intermediate to be mimicked, and then to the reactants. Reactions that involve Diels-Alder [4+2] cycloadditions provide illustrative examples of the general concept through the reactive intermediate stage of the overall reaction.

The reactants of a generalized Diels-Alder [4+2] cycloaddition reaction are a dienophile molecule and a conjugated diene. The reactants (substrates) of the Diels-Alder [4+2] cycloaddition reaction catalyzed herein are somewhat more circumscribed.

First, the reactants must be soluble in the liquid reaction medium (composition) in which the reaction is carried out. Where an aqueous composition is utilized, organic solvents such as acetonitrile, methanol, dimethyl formamide (DMF) or dimethyl sulfoxide (DMSO) can be present in that composition to assist in solubilizing the reactants. When present, organic solvents usually constitute up to about 20 volume percent, and preferably about 5 to about 10 volume percent of the otherwise aqueous, liquid composition. However, the reactions contemplated herein can also be carried out in substantially anhydrous apolar organic solvents such as octane or benzene as described in Kilbanov, *CHEMTECH*, June 1986:354–359, or in reverse micelles as described by Dufor et al., *J. Am. Chem. Soc.*, 110:8713–8714 (1988); Russell et al., *Biochem. Biophys. Res. Comm.*, 158(1):80–85 (1989); and Luisi, *Angew. Chem., Int. Ed. Engl.*, 24(6):429–528 (1985), all of whose disclosures are incorporated by reference.

The conjugated diene molecule is cyclic and contains a five- or six-membered ring that includes the reactive conjugated double bonds as well as a fugitive leaving group. The fugitive leaving group is a moiety, which, when present in the cyclic conjugated diene, is substantially stable; i.e., the compound can be made and used without decomposition, but which, after completion of the Diels-Alder [4+2] cycloaddition reaction to form the reactive intermediate is capable of expulsion as a molecular entity, typically a gas, from the reactive intermediate in forming the reaction product. Exemplary fugitive leaving groups that form gases include $-SO_2-$, $-N{=}N-$, $-CO_2-$ and $-HC{=}N-$, that form $SO_2$, $N_2$, $CO_2$ and HCN or a nitrile, respectively, upon expulsion from the reactive intermediate.

The dienophile molecule is less circumscribed in structure. That molecule need only have the requisite solubility in the composition and contain a reactive multiple bond; i.e., the bond that reacts with the conjugated diene bonds. A reactive double bond is typically and preferably olefinic (ethylenic), but need not be so, and compounds containing the following double bonds can be utilized as the dienophile: $-N{=}N-$; $-N{=}C{=}$, $O{=}N-$ and ${=}C{=}O$. The dienophile can also be a triple bond so that molecules with $-C{\equiv}C-$ and $-C{\equiv}N$ groups can be useful dienophiles, as can compounds that contain two double bonds such as cyclopentadiene.

It is contemplated for the reactions discussed herein that both the cyclic diene and the dienophile molecules contain one or more substituent groups in addition to the endocyclic conjugated double bonds and fugitive leaving group of the cyclic diene molecule and the reactive multiple bond of the dienophile. Thus, unless specifically noted to the contrary, each cyclic diene and dienophile molecule is a substituted compound; i.e., is a derivative of a parent compound.

Typically, at least one of the diene molecule and the dienophile molecule utilized contains one or more substituents that "activate" the molecule toward reaction, although in some instances one or both molecules contain a "deactivating" substituent or substituents. The Diels-Alder [4+2] cycloaddition reaction is generally considered to be a concerted reaction, and as such, either molecule of the reactants can be the "electron donor" or "electron acceptor", depending upon the substituents bonded thereto.

Since the reaction is a donor-acceptor reaction, both reactants generally do not have electron donating substituents such as alkyl groups bonded to them, nor do both generally have electron withdrawing groups such as carbonyl groups bonded to them unless the uncatalyzed reaction needs to be slowed, or because one of the substituent activating or deactivating groups is itself desired for another synthetic reason. Preferably therefore, one reactant contains one or more electron-donating substituents whereas the other contains one or more electron-withdrawing substituents. Thus, more than one substituent; i.e., a plurality of substituents, of a particular type can be bonded to either molecule, as can mixtures of substituents. Exemplary diene and dienophile molecules and their activating groups are discussed hereinafter.

Another feature of the reactions of interest herein is that the reaction product contains one double bond more than is present in the reactive intermediate. The additional double bond is formed upon expulsion of the fugitive leaving group and rearrangement of the resulting bonds. Because of the cyclic character of the conjugated diene and the 1,4-bonding of the dienophile to the cyclic conjugated diene, the reaction product is itself also a cyclic conjugated diene that can contain five or six atoms in its ring.

The reactive intermediate and immunizing and antigenic haptens additionally contain a [2.2.1] or [2.2.2] bicyclic ring system including the fugitive leaving group and isostructural moiety, respectively, that are not present in the reaction product. Thus, if the reaction product is unicyclic, the reactive intermediate and hapten are bicyclic; and if the reaction product is bicyclic, the reactive intermediate and hapten are tricyclic, and so on, with one of the reactive intermediate and hapten ring systems being a [2.2.1] or [2.2.2] bicyclic ring system.

As already noted, each of the cyclic diene and dienophile molecules typically has one or more substituent groups. Those substituent groups are also present in the reactive intermediate and are usually also present in the cyclic reaction product. Where a nitrile derivative is the fugitive leaving group, a substituent present in the reactants can be lost from the cyclic reaction product as part of that fugitive leaving product.

Inasmuch as the reactants and reactive intermediate include one or more substituent groups, one or more substituent groups that individually substantially correspond to the individual substituent group or groups present in the reactants and reactive intermediate are also present in the immunizing and antigenic haptens. That substantial correspondence of substituents and their locations, the isostructural relation between the fugitive leaving group and the corresponding moiety in the hapten (discussed hereinafter) and the sameness of the bicyclic ring structures present in the reactive intermediate and hapten (also discussed hereinafter) define the isologous relation between the reactive intermediate and hapten.

It is preferred, although not required, that one or more substituents present in the reactant cyclic diene and dienophile molecules and the reactive intermediate be identical to the one or more substituents present in the immunizing and antigenic hapten molecules. Indeed, because the hapten molecule includes a group to link it to an immunogenic carrier to induce the catalyst molecules that is usually not present in the reactant molecules, complete identity of substituents is rare.

Where the one or more substituents are not identical between reactants and hapten, it is preferred that the hapten substituent be isostructural and larger in size than the corresponding substituent(s) of the reactant. Thus, for example, where the reactant contains a straight chain substituent, the hapten also contains a straight chain substituent of about the same length to several atoms longer. An example of this type of substantial correspondence is illustrated hereinafter where the studied reactant contained an ethyl group whereas the immunizing and antigenic haptens contained a carboxypentyl group.

The configuration of substituent groups in the reaction product also plays a role in selecting an appropriate immunizing hapten's structure. An antibody combining site can be exquisitely selective in its binding properties or less so, depending upon the screening criteria utilized by the skilled worker. For example, Tramontano et al, *Proc. Natl. Acad. Sci. USA*, 83:6736-6740 (1986) reported that a catalytic antibody could distinguish between an N-acetyl and an N-trifluoroacetyl group in otherwise identical ester molecules and cleave one, but not the other. On the other hand, Houghten, *Proc. Natl. Acad. Sci. USA*. 82:5131-5135 (1985) reported the preparation of 248 thirteen-residue polypeptides in which each position of the polypeptide was successively replaced with each of the twenty naturally occurring L-amino acid residues. That paper reported that a monoclonal antibody raised to the original polypeptide immunoreacted similarly with all of the polypeptides except those in which a particular aspartic acid residue was exchanged for another residue.

As a consequence of the specificity of a paratope of a catalyst molecule, a particular, preselected reaction product can be produced in an increased proportion up to substantial exclusivity as compared to the proportion of that product formed in an uncatalyzed reaction. Here, working backward from the position of a substituent in a preselected reaction product, the skilled worker can determine a corresponding structure for the reactive intermediate and then the structures of the reactants required for the reaction. It is noted that the proportion of both stereoisomers and structural isomers can be increased as discussed hereinafter.

With the above in mind, the skilled worker can thus go about constructing the immunizing hapten that is an analog to the transition state for the formation of the reactive intermediate leading to the reaction product.

The immunizing hapten is synthesized to contain a [2.2.1] or [2.2.2] bicyclic ring system as is present in the corresponding reactive intermediate, and at least one fewer double bonds than are present in the reaction product. That hapten also contains a substituent (or more) in a structural position(s) that corresponds to the same substituent position(s) in the reactive intermediate and reaction product. The hapten further includes a means such as a carboxyl- or amine-containing group to link the hapten to an immunogenic carrier because the hapten, by definition, is itself not capable of inducing antibody production.

The immunizing hapten and reactive intermediate are thus substantially similar in size and shape, are isologous, but differ in two major respects. First, the hapten has a carrier linking group generally not present in the reactive intermediate. Second, although both contain one [2.2.1] or [2.2.2] bicyclic ring system not present in the reaction product, one ring of that bicyclic ring system of the reactive intermediate includes the fugitive leaving group, whereas the corresponding ring in the hapten contains a group or moiety that is isostructural to the fugitive leaving group and is substantially less reactive in the hapten than is the fugitive leaving group in the reactive intermediate.

The term "isostructural" is used herein to mean that where the fugitive leaving group forms a five- or six-membered ring portion of a before-mentioned [2.2.1] or [2.2.2] bicyclic ring system in the reactive intermediate, an analogous ring is present in the hapten. Still further, in preferred practice, the bond lengths of one ring of the analogous bicyclic ring (the ring with the moiety isostructural to the fugitive leaving group) present in the hapten are slightly longer than are those of the fugitive leaving group or the total volume of the isostructural analogous ring of the hapten is slightly larger than is that of the fugitive leaving group.

For example, a —CCl$_2$— group is isostructural to a —SO$_2$— fugitive leaving group, and the calculated bond lengths for the C-CCl$_2$ and C-Cl bonds are somewhat longer than are the calculated bond lengths for C-SO$_2$ and S-O. Additional isostructural groups for a hapten and fugitive leaving group include a —CH$_2$—CH$_2$—, —CH$_2$—S—, —S—S— or —CH$_2$—NH— group and a —N=N— fugitive leaving group, and a —CH$_2$—C(O)— or —CH$_2$—C(S)— group and a —O—CO— fugitive leaving group, and a —CH=CH—, —CH$_2$—S—, —S—S—, —CH$_2$—NH—, or —CH$_2$—CH$_2$— group and a —CH=N— fugitive leaving group.

In other instances, it is synthetically convenient to utilize two isostructural moieties in a hapten. For example, a —HC=CH— group is isostructural to a —HC=N— fugitive leaving group, and it can be convenient to utilize a —CH$_2$— group in a hapten instead of an —O— group that is present in the reactive intermediate.

III. The Diene and Dienophile Molecules

The conjugated cyclic diene molecule contains a five-membered or a six-membered ring that includes the reactive conjugated double bonds as well as the fugitive leaving group. Exemplary five- and six-membered ring-containing conjugated dienes that also contain a fugitive leaving group include substituted oxazoles, α-pyrones, thiophene dioxides, pyrimidines, pyridazines, pyrazines, 1,2,3-triazines, 1,3,5-triazines, 1,2,4-triazines and 1,2,4,5-tetrazines.

The expelled leaving group from the above compounds can be a function of the substitution of the conjugated cyclic diene molecule, and sometimes also a function of the structure of the dienophile. For example, when reacted with a substituted ethylenic dienophile, a reactant oxazole derivative can expel water or an alcohol in a "complex" fragmentation reaction as discussed previously, depending upon the other substituents present, whereas when reacted with a substituted acetylenic dienophile, a nitrile or hydrogen cyanide can be expelled in a "simple" fragmentation reaction. Derivatives of thiophene dioxide expel $SO_2$, whereas α-pyrone and its derivatives expel $CO_2$. Substituted pyrimidines, pyrazines, 1,3,5-triazines and 1,2,4-triazines expel a nitrile or hydrogen cyanide. Substituted pyridizines, 1,2,3-triazines and 1,2,4,5-tetrazines expel nitrogen, as can also 1,2,4-triazines.

Diels-Alder reactions of derivatives of the above conjugated cyclic dienes that can be catalyzed as discussed herein are discussed in Boger, *Chem. Rev.*, 86:781-793 (1986); Raasch, *J. Org. Chem.*, 45:856-867 (1980); Raasch, *J. Org. Chem.*, 45:867-870 (1980); and Jacobi et al, *J. Org. Chem.*, 46:2065-2069 (1981), whose disclosures are incorporated by reference. The reaction products described in those publications that can be formed using a catalyst and method as disclosed herein include several useful materials, as well as reaction products that are intermediates for the preparation of useful materials such as ellipticine, streptonigrin, lavendamycin, (±)-ligularone, (±)-petasalbine, (±)-paniculide A, (±)-gnididione, (±)-isognididione and pyridoxal (vitamin $B_6$).

The structure of the multiple bond-containing dienophile molecule is much less constrained, as noted before. Straight, branched chain and cyclic dienophiles are contemplated as are well known.

The use of a reacting double bond in the dienophile results in the formation of a cyclic reaction product having five or six atoms in the ring and two endocyclic conjugated double bonds, whereas use of a reacting triple bond dienophile usually leads to a six-membered ring aromatic reaction product having three conjugated endocyclic double bonds, although five-membered ring compounds having two endocyclic conjugated double bonds can also be formed, as is known. Thus, the reaction product is cyclic, and contains at least two conjugated double bonds. Dienophiles containing ethylenic double bonds and acetylenic triple bonds are preferred herein.

It is also to be noted that the reactive multiple bond of the dienophile is not limited to that of ethylene and acetylene and their derivatives. Thus, —N=N—, —N=O, =C=O, =C=N— and —C≡N are also contemplated dienophile reactive multiple bonds, as noted previously and are disclosed in D.L. Boger and S.N. Weinreb, *Hetero Diels-Alder Methodology In Organic Synthesis*, Academic Press, San Diego, Calif. (1987).

It should further be noted that the cyclic conjugated diene and dienophile can be linked together in the same molecule [Boger, *Chem. Rev.*, 86:781-793 (1986)], so that the initial Diels-Alder [4+2] cycloaddition fragmentation/reaction is intramolecular. For ease of expression, however, the cyclic conjugated diene portion and the dienophile portion of such a single molecule are considered herein to be separate reactant molecules.

Each of the cyclic conjugated diene and multiple bond-containing dienophile is usually utilized in a substituted form; i.e., as a derivative of the parent compound, as noted previously. The substituent selected for either molecule can be present as an activating or deactivating group that is later removed or replaced, as an ultimately desired substituent, to help assist in stereo- or regioselectivity, and the like, as are well known.

Using as exemplary the before-mentioned heterocyclic azadienes (e.g., oxazole, pyrimidines, pyridazines, triazines and tetrazines) that themselves react as electron-deficient cyclic dienes in the reactions of interest, the following observations generally hold: (1) an added electron withdrawing substituent accents the electron-deficient character of the derivatives and permits reactions with electron-rich dienophiles; (2) substitution with strong electron-donating substituents can overcome the electron-deficient character of the heterocyclic azadienes to permit reaction with usual electron-deficient dienophiles; and (3) entropic assistance provided by an intramolecular Diels-Alder [4+2] cycloaddition fragmentation/reaction can override the otherwise reluctant participation of otherwise unactivated heterocyclic azadiene molecules [Boger, *Chem. Rev.*, 86:781-793 (1986)]; that entropic effect being similar to the entropic assistance provided by a useful catalyst molecule described herein.

As noted previously, the rate of the first reaction, the Diels-Alder [4+2] cycloaddition, can be accelerated by the use of substituents that activate the reactant pair by making one of the diene or dienophile molecules more electron-deficient and the other more electron-rich; i.e., by using electron-withdrawing substituents on one molecule and electron-donating substituents on the other. The reactant pair can be deactivated toward the reaction by use of electron-withdrawing substituents or electron-donating substituents on both the diene and dienophile.

Exemplary electron-withdrawing groups (substituents) are those that exhibit positive Hammett sigma values relative to hydrogen for meta substituents. Convenient lists of such substituents can be found in J. Hine, *Physical Organic Chemistry*, 2nd ed., McGraw-Hill Book Co., Inc., New York, page 87 (1962) and in *Correlation Analysis in Chemistry Recent Advances*, N.B. Chapman and J. Shanger eds., Plenum Press, New York (1978). Electron-withdrawing substituents can also be identified by the change in chemical shift observed in nuclear magnetic resonance (NMR) for protons due to the presence of the substituent. Electron-withdrawing groups typically induce down field shifts in the resonance position of a selected proton. Exemplary lists of chemical shifts induced by various substituent groups can be found in R.M. Silverstein and G.C. Bassler, *Spectromeric Identification of Organic Compounds*, John Wiley and Sons, Inc., New York, pages 71-89 (1964).

Exemplary electron-donating substituent groups exhibit negative Hammett sigma values relative to hydrogen for meta substituents, and tend to induce an up field shift of proton resonance in NMR. The before-mentioned lists also include values for electron-donating substituents.

The electron-withdrawing or electron-donating effect of a given substituent on the diene or dienophile is typically exerted by a substituent group located within one atom (alpha) of the reactive multiple bond to which it is directly linked. That is, the electron-donating or electron-withdrawing substituent group is bonded directly to a reactive double or triple bond of the diene or dienophile, and is located alpha to the nearest atom of that unsaturated bond; i.e., bonded directly to one atom of the multiple bond.

Exemplary electron-withdrawing substituent groups include the carbonyl group of an aldehyde, ketone, acid, ester, or amide, a nitrile, nitro, halo, a substituted or unsubstituted aryl group, a hydroxy-methyl, amino- or substituted-aminomethyl, cyanomethyl, halomethyl and vinyl group. Exemplary electron-donating substituent groups include straight chain, branched chain and cyclic alkyl, amino, substituted amino, hydroxy and ether groups. Still further electron-withdrawing and electron-donating substituent groups should be apparent to a skilled worker from the exemplary lists noted before.

A useful substituent group typically contains a single atom as in hydrogen or a halogen, as well as a group, chain or ring system that can contain up to about fifteen atoms linked together in the group, chain or ring (for a total of up to about fifty atoms in the substituent). Still larger substituent groups, as where reaction products containing multiple rings are prepared, can also be utilized, but are often less convenient to prepare, as are the corresponding haptens. Where the diene and dienophile are part of the same molecule and the Diels-Alder [4+2] cycloaddition fragmentation/reaction is intramolecular, the group linking the diene and dienophile can be viewed as a combined substituent of both portions, and the substituent atoms present are therefore summed.

Exemplary specific substituent groups include hydrogen, halogen (fluoride, chloride, bromide and iodide), $C_1$–$C_6$ lower alkyl and substituted $C_1$–$C_6$ lower alkyl such as methyl, ethyl, sec-butyl, hexyl, cyclopentyl, cyclohexyl, 3-methyl cyclopentyl, 1-chloroethyl, hydroxy methyl, tri-fluoromethyl groups; amino, mono- and di-$C_1$–$C_6$ lower alkyl, benzyl and phenyl amino and cyclic amino such as methylamino, methylisopropylamino, cyclohexylamino, monopholino, pyrrolidino, anilino, p-methoxyanilino, benzyl methylamino and m-nitrobenzylamino groups; $C_1$–$C_6$ lower alkyl, phenyl, substituted phenyl, and benzyl carboxylate (ester) such as methoxy carbonyl, butoxy carbonyl, isopropoxy carbonyl, cyclopentoxy carbonyl, phenoxy carbonyl, p-nitrophenoxy carbonyl, and 3-methyl benzoxy carbonyl groups; $C_1$–$C_6$ lower alkyl, phenyl, substituted phenyl, benzyl and substituted benzyl carbonyl (ketone) such as methyl carbonyl, ethyl carbonyl, sec-butyl carbonyl, cyclohexyl carbonyl, phenyl carbonyl, 3-chlorophenyl carbonyl, and (2-ethyl)benzyl carbonyl groups; carboxamide in which the amine portion is unsubstituted or substituted as discussed above to provide N-methyl carboxamide, N,N-methylisopropyl carboxamide, N-cyclohexyl carboxamide, pyrrolidinyl carboxamide, morpholinyl carboxamide, carboxanilide, carbox(p-methoxy) anilide, N,N-benzylmethyl carboxamide and m-nitrobenzyl carboxamide groups; phenyl and substituted phenyl such as phenyl and p-trifluoromethyl phenyl groups; and $C_2$–$C_6$ lower alkenyl groups such as vinyl, 2-propenyl, 3-cyclohexenyl and 2-methyl-3-butenyl.

It is also noted that the dienophile can also be a single or fused ring compound. In such an instance, the substituent groups bonded to the atoms of the reacting unsaturated bond are considered to be joined to form the ring.

The ring or fused rings of the dienophile can be carbocyclic or heterocyclic, and can be substituted or unsubstituted. Exemplary ringed unsaturated dienophile molecules include maleic anhydride, maleimide, N-alkyl maleimides such as N-ethyl, N-methyl and N-(5-carboxy)pentyl maleimides, 1,4-benzoquinone, 1,4-naphthoquinone, indole, cyclopentadiene and carbomethoxy cyclopentadiene.

Using ethylenic double bonds as exemplary for both the diene and dienophile molecules, and a group Y as a before-mentioned fugitive leaving group, exemplary reactants have structures that correspond to the formulas for the dienophile and diene, respectively:

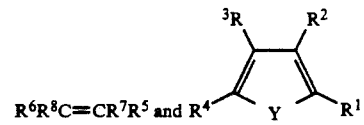

The reactive intermediate and hapten (immunogen or antigen) have structures that correspond respectively to the following formulas:

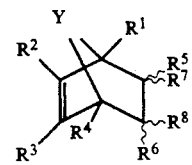

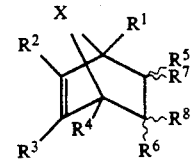

wherein X is isostructural to the fugitive leaving group Y.

In the above formulas, $R^1$, $R^2$, $R^3$, $R^4$, $R^5$, $R^6$, $R^7$ and $R_8$ are independently selected from the before-discussed substituent groups, or $R^5$ and $R^6$ are absent and are replaced by a bond between the two carbon atoms shown, making the dienophile an acetylene derivative, and one of $R^{1-8}$ in the hapten is adapted for linking the hapten to an immunogenic carrier molecule as with an amine, hydroxyl, mercaptan or carboxyl group. It is also noted that no stereochemistry is meant to be implied by the above-drawn structures, and thus wavy lines are utilized to illustrate bonding to the bicyclic ringed reactive intermediate and hapten for $R^{5-8}$.

Preferably, $R^1$, $R^2$, $R^3$, $R^4$, $R^5$ and $R^6$ are independently selected from the group consisting of hydrogen, halogen, $C_1$–$C_6$ lower alkyl (including straight and branched chains and cyclic groups), $C_1$–$C_6$ lower alkyl carbonyl (ketones), $C_1$–$C_6$ lower alkoxy carbonyl (esters), mono-$C_1$–$C_6$ and di-$C_1$–$C_6$ lower alkyl substituted amino carbonyl (amide), amino carbonyl itself, phenyl, substituted phenyl, amino (-$NH_2$) and mono-$C_1$–$C_6$ and di-$C_1$–$C_6$ lower alkyl substituted amino, hydroxyl, $C_1$–$C_6$ lower alkoxy and phenoxy or substituted phenoxy substituent groups, or $R^5$ and $R^6$ are absent and are replaced by a bond between the two carbon atoms shown, making that dienophile a derivative of acetylene. $R^7$ and $R^8$ preferably each contain a total of 1 to about 50 atoms, and each is selected from the group consisting of hydrogen, an electron-withdrawing group relative to hydrogen, and an electron-donating group relative to hydrogen, or $R^7$ and $R^8$ together form a ring containing up to eight atoms. Preferably, only one of $R^7$ and $R^8$ is hydrogen. In particularly preferred practice, $R^7$ and $R^8$ form a substituted heterocyclic ring containing five atoms.

IV. Catalyst Molecules

The present invention contemplates a before-described catalyst molecule. Such a catalyst molecule comprises an antibody combining site-containing molecule, preferably monoclonal, such as a whole antibody, an F(ab') portion of an antibody molecule or a recombinant antibody combining site-containing molecule.

The catalyst molecule catalyzes a Diels-Alder [4+2] cycloaddition reaction between a dienophile molecule containing a reactive multiple bond and a conjugated diene molecule to form a cyclic reaction product whose formed ring contains five or six atoms and at least two conjugated double bonds. The dienophile and diene are as discussed previously, the diene having a structure that includes a five- or six-membered ring and a fugitive leaving group.

In addition to catalyzing the above reaction, the catalyst molecule immunoreacts with an antigen whose structure (i) includes a [2.2.1] or [2.2.2] bicyclic ring system that is absent from the reaction product and (ii) contains at least one endocyclic double bond fewer in that bicyclic ring system than the number of endocyclic double bonds present in the reaction product. Thus, the catalyst molecule immunoreacts with an antigen that is isologous to the reactive intermediate formed by the Diels-Alder reaction.

The catalyst also binds to (immunoreacts with) the diene and dienophile reactant molecules. That immunobinding is typically difficult to detect, and is usually best detected by the fact that the reaction product is formed.

The catalyst molecule is preferably a whole, intact monoclonal antibody molecule. The dienophile molecule is preferably cyclic and includes an electron withdrawing substituent moiety relative to hydrogen that is located alpha to the reactive multiple bond. It is also preferred that the fugitive leaving group form a gaseous compound upon the formation of the reaction product.

An exemplary monoclonal catalyst molecule designated 1E9 secreted by hybridoma 1E9 was prepared and utilized to catalyze a Diels-Alder [4+2] cycloaddition reaction. Details for the preparation, characterization and reactions of that catalyst molecule are discussed hereinafter.

Depending upon the reaction selected for catalysis and the selected catalyst molecule, some reactive amino acid residue side groups can require protection so that the catalyst molecule does not irreversibly react with one or both of the reactants, the reactive intermediate or the reaction product. Such protection is readily carried out using well known techniques.

For example, reactive lysine and N-terminal amino groups can be reductively alkylated using an aldehyde such as formaldehyde or acetaldehyde or a ketone such as acetone and a reducing agent such as sodium cyanoborohydride following the procedures discussed in Jentoft et al., *J. Biol. Chem.*, 254:4359–4365 (1979). Other reactive side groups such as hydroxyl, mercaptan, histidyl and carboxyl groups can be similarly protected if desired and/or necessary using reactions well known in the art. R.L. Lundblad and C.M. Noyes, *Chemical Reagents for Protein Modification*, Vols. 1 and 2, CRC Press, Inc., Boca Raton, FL (1984).

The use of such protecting groups on a catalyst molecule does not substantially affect its previously discussed binding properties in regard to the antigen, nor its catalytic properties toward the reactants. In addition, such reactions with protecting groups do not alter the fact that a specific, useful catalytic molecule such as monoclonal antibody 1E9 is secreted by a particular hybridoma or as prepared and expressed by recombinant DNA technology using a particular vector or construct and expression host.

V. Methods

Another aspect of this invention is a method of catalyzing the formation of a before-discussed reaction product having a five- or six-membered ring that includes at least two conjugated endocyclic double bonds. That method includes the steps of (a) admixing a dienophile molecule having a reactive multiple bond and a conjugated diene molecule having a structure that includes a fugitive leaving group within a five- or six-membered ring with a before-described catalyst molecule in a liquid composition to form a reaction mixture; and (b) maintaining the reaction mixture for a time period sufficient for the reaction mixture to form. Where the liquid composition is an aqueous composition, the maintenance step is carried out under biological conditions, as discussed previously. The reaction product so formed is preferably recovered in a subsequent step.

The reactants and catalyst molecule utilized are as discussed previously.

The reaction product contains at least two conjugated endocyclic double bonds. A five-membered ring can contain only two such bonds. A six-membered ring can contain three such bonds, and if so, is an aromatic compound such as a benzene, pyridine or pyrimidine derivative. Carbocyclic and heterocyclic reaction products are thus contemplated.

Where the dienophile contains a reactive triple bond, as is present in an acetylene derivative, the reaction product is a generally six-membered ring, aromatic compound, although cyclic dienes can also be formed from such reactions. Where the reaction product is a six-membered ring and the dienophile contains a reactive double bond, a conjugated hexadiene is the reaction product.

A cyclohexadiene reaction product can usually be recovered from the reaction mixture. This is the case particularly where the reaction mixture is kept anaerobic or oxidizing agents other than atmospheric oxygen are excluded from the reaction mixture.

It is often desired, however, to obtain the corresponding aromatic product derived from a substituted cyclohexadiene (cyclohexadiene derivative including aza-substituted rings) reaction product. In that instance, the reaction mixture can be stirred in the presence of air, oxygen can be bubbled through the reaction mixture during or at the completion of the reaction, or another oxidizing agent such as hydrogen peroxide can be added to the reaction mixture.

A further aspect of this method embodiment of the invention is a method for increasing the proportion of a preselected reaction product formed in Diels-Alder [4+2] cycloaddition/fragmentation reaction to form a plurality of reaction products. Such reactions have been generally discussed previously herein. The reaction product whose relative proportion is enhanced can be a stereoisomer or a structural isomer.

Where both reactants are symmetrically substituted, no structural isomers are possible. When either or both of the diene and dienophile molecules is asymmetrically substituted, regio- or structural-isomers can be formed.

Hexocyclic diene reaction products can also form stereoisomeric pairs so long as the dienophile does not contain four identical substituent groups.

Thus, taking as exemplary a monosubstituted cyclic diene having its substituent bonded to one of the same atoms as the fugitive leaving group and a monosubstituted dienophile as reactants, and a hexocyclic diene derivative as reaction product, the six-membered ring cyclohexaidene derivative reaction product could have the two substituents bonded to adjacent ring atoms, or those substituents could be separated by one ring atom. In an uncatalyzed reaction, various steric, electronic, kinetic, thermodynamic and possibly ionic factors could decide which of the two possible structural isomers would predominate, if not be the only reaction product observed.

Because of the catalysis exerted by a catalyst molecule of this invention, the usually seen proportion of such isomers can be changed so that a normally less favored product is formed in greater yield or so that the usually favored product is formed in higher yield. In addition, where the catalyzed rate of formation of the desired reaction competes favorably with the uncatalyzed rate of the undesired reaction, the desired, preselected reaction product can be formed to the exclusion of the undesired product.

The desired result is preferably obtained by selection of the immunizing or screening haptens. Thus, an immunizing hapten having a structure isologous to the reactive intermediate leading to the desired structural isomer of the reaction product is utilized to induce production of the antibody catalyst. Alternatively, a mixture of haptens having structures isologous to the desired and non-desired reactive intermediate is used to induce the antibodies, but only those antibodies that immunoreact with the hapten of the desired structure as antigen are utilized to catalyze the reaction.

Thus, as noted previously, the structure of the immunizing hapten that is isologous to the Diels-Alder [4+2] cycloaddition reactive intermediate flows backward from the structure of the reaction product, and its isomers, through the reactive intermediate, to the transition state for bond formation to be mimicked, and then to the reacting diene and dienophile molecules. That immunizing hapten can be used as an antigen to screen the antibodies produced, and is preferably so used or another hapten having the same structure is used as the screening antigen.

As discussed before, a mixture of isomeric haptens can be used in the immunization and a single hapten of the appropriate structure utilized as the screening antigen. Still further, an immunizing hapten having the desired structure can be utilized to induce the antibodies, whereas another stereoisomer of that immunizing hapten is used as an antigen to screen the induced antibodies for those that bind to it and therefore lead to the preselected reaction product.

Here, for increasing the proportion of a preselected regioisomeric reaction product, the method steps are similar to those discussed before except that (a) at least one of the dienophile and diene molecule reactants must be asymmetrically substituted, and (b) the catalyst molecule additionally binds to an antigen that contains a substituent that is the same as or corresponds substantially to the asymmetric substituent, and that substituent is at an analogous location in the preselected reaction product. The "analogous location" is the position in the reactive intermediate the gives rise to the ultimate location of the substituent in the reaction product.

Diels-Alder [4+2] cycloadditions proceed by a cis addition mechanism. The bicyclic reactive intermediate formed in the reactions of interest here can be the result of an endo or exo cis addition, although endo products are normally favored. Once the reaction product is produced from such a reactive intermediate, cis alpha, alpha or beta, beta substituents can result. Preparation and use of an immunogenic or screening hapten as described before having either preselected stereoconfiguration can therefore lead to preferential preparation of either type of isomeric reaction product.

The before-discussed structural isomers can also exist as the stereoisomers above. As a consequence, use of an immunizing or screening hapten that not only has the desired, preselected regioconfiguration, but also contains those substituents in desired stereoconfiguration can lead to a desired stereoisomer of the preselected structural isomer.

For increasing the proportion of a preselected stereoisomer, two types of reaction are contemplated. In a first reaction, enantiomers are formed at the ring atoms of the cyclic reaction product that are contributed by the dienophile. In the second type of reaction, either the dienophile or diene reactant molecules, or both, contains a chiral center on one or more of its substituents groups and that reactant is racemic so that enantiomeric or diastereomeric cyclic reaction products can be formed. Methods for preparing a preselected stereoisomer or of enhancing the proportion of one such isomer relative to other such isomers are discussed below.

In the first reaction type, where enantiomeric stereoisomers are formed at the reaction product ring atoms contributed by the dienophile, the reaction product must be a cyclic six-membered ring compound having endocyclic, conjugated double bonds (a derivative of cyclohexadiene). The six-membered ring stereoisomeric product need not be carbocyclic, but at least one carbon atom, and preferably two carbon atoms are present constituting the formed saturated endocyclic bond and a tetrahedral carbon atom about which the stereoisomers are formed. The reactive multiple bond of the dienophile must be a double bond, one of whose atoms is carbon. Preferably, both atoms of the double bond are carbon.

In addition, therefore, the catalyst molecule binds to an antigen that also mimics the stereochemistry of the preselected stereoisomer; i.e., has an isologous stereoconfiguration to the reactive intermediate and reaction product. That is, the substituent(s) substantially corresponding to or the same as the substituent(s) of the dienophile are present in the antigenic bicyclic hapten (and reactive intermediate) in an endo configuration where the substituent(s) of the preselected reaction product is in the α-configuration and in the exo configuration where the substituent(s) of the preselected reaction product is in the β-configuration. The substituent or substituents of the antigenic hapten are thus the same as or correspond substantially to the asymmetrically substituted substituent or substituents present in the dienophile molecule, and the substituent or substituents are present at an analogous location and stereoconfiguration in the preselected reaction product.

Thus, where the carbon-containing reactive double bond of the dienophile molecule is asymmetrically substituted with at least one carbon atom of that double bond having two different substituents and the cyclic diene molecule is symmetrically substituted, enantiomeric cyclohexadiene derivatives can form. Where the reactive double bond contains two carbon atoms, one of those two carbon atoms can contain two identical substituents so long as the other carbon atom of that double bond does not.

In a catalyzed reaction according to this aspect of the method embodiment of the invention, using a catalyst molecule as described herein, one or the other of those two enantiomers can be preselectedly formed in preference to the other enantiomer; i.e., the relative proportion of one enantiomer can be increased relative to the other. Alternatively, using the broader aspect of the method embodiment, both of the enantiomers can be formed. The difference between the broader and narrower aspects of the method resides in the catalyst molecule selected for use.

Enantiomeric stereoisomers are also formed where one or more substituent groups or either of the diene or dienophile molecule reactants contains a chiral center. So long as that chiral center is bound by the antibody combining site of the catalyst molecule, one or the other of the enantiomeric cyclic reaction products can be formed in preference to the other; i.e., the proportion of a preselected enantiomeric reaction product formed can be increased relative to the other enantiomer where the chiral reactant is racemic.

Where the cyclic diene molecule is asymmetrically substituted and the carbon-containing reactive double bond of the dienophile molecule is asymmetrically substituted as discussed above, enantiomeric structural isomers can be formed. In a reaction catalyzed according to this aspect of the method embodiment of the invention, a preselected one or the other of the enantiomers of a preselected structural isomer can be preferentially formed; i.e., its relative proportion increased by use of a catalyst molecule that immunoreacts with an antigen that is structurally isologous to the reactive intermediate that fragments to form the desired cyclic reaction product. Again, both enantiomers can also be formed, if desired, depending on the catalyst molecule selected for use.

A preselected diastereomeric reaction product can also be preferentially formed by a method of this invention. Here, at least one of the substituent groups of the cyclic diene molecule or of the dienophile molecule includes an optically active isomer or a pair of enantiomers. When such reactants are reacted as described before for preparation of a selected stereoisomer (enantiomer), diastereomeric reaction products can be formed, and the proportion of one enantiomeric pair of diastereomers or a single enantiomeric diastereomer can be increased using a before-described method. In this case, the cyclic reaction product can contain a five- or six-membered ring.

Thus, in either type of reaction in which a preselected stereoisomer is preferentially formed, the reactant diene and dienophile molecules include one or more substituent groups that give rise to stereoisomeric cyclic reaction products. The antigen bound by a catalyst molecule in such instances contains one or more substituents that correspond substantially to, or are preferably the same as, the substituent or substituents present in the reactant molecules, and which substituent or substituents are present at an analogous location and stereoconfiguration in the preselected reaction product.

Where the preselected reaction product is both a possible stereoisomer and a regioisomer, the before-discussed conditions for both such types of product must be met simultaneously by the reaction product, the reactants and the catalyst, as well as the antigen to which the catalyst binds (or with which it immunoreacts).

A before-described method can also be carried out with the catalyst molecule immobilized on a solid phase support. The reaction can be carried out in a column of the immobilized catalyst, for example by adding a solution of the reactants at the top of the column and recovering the reaction product-containing solution from the bottom of the column. Here, the liquid composition is formed when the reactant-containing solution contacts the immobilized catalyst. The reaction can also be carried out in standard laboratory glassware such as a beaker or flask by simply swirling the immobilized catalyst in the reactant-containing liquid composition. This type of reaction is particularly useful when the reaction product is soluble in the liquid composition because the solid phase-linked catalyst molecules can be readily separated from the liquid composition by filtration, centrifugation or the like.

Where reactions are carried out in an aqueous composition, the catalyst molecule is linked to a water-insoluble solid phase matrix as is used to form an affinity solvent. Such solid phase sorbents are known in the art and their methods of preparation are well known.

Every material has at least some water-solubility. As a consequence, the term "water-insoluble" is used herein in its usual sense to mean that the matrix and immobilized catalyst made therefrom are recovered substantially intact and in substantially the same amount as admixed with the aqueous medium when the reaction is carried out. The matrix is typically swellable in water, and can form a gel-like solid phase and still be within the purview of a water-insoluble material as contemplated herein.

A particularly preferred immobilized catalyst contains a before-described catalyst molecule linked to a particulate water-insoluble matrix comprised of cross-linked agarose. Particularly preferred is a cross-linked agarose such as cyanogen bromide-activated Sepharose 4B-CL (Pharmacia Fine Chemicals, Piscataway, N.J.) which is readily linked to amine-containing materials such as the present catalyst molecules to form the solid phase immobilized catalyst.

Sepharose 4B-CL is utilized herein as an exemplary solid phase matrix. However, additional particulate and monolithic solid phase matrices are also useful herein. Exemplary of such matrices are Sepharose 6B and 4B, glass beads, and the inner and outer surfaces of hollow fibers as are useful in hemodialysis or ultrafiltration. In addition to matrices specifically mentioned herein, several suitable particulate (beaded) matrices are listed in the 1984 Sigma Chemical Company catalogue at pages 98 to 113. Typically, any water-insoluble solid phase matrix that reacts with an amino groups or a carboxy group is suitable.

Methods of affixing a catalyst molecule to the matrix are also well known by skilled artisans and need not be dealt with in detail herein. Illustratively, however, such methods include use of activated carboxyl groups as are provided by cyanogen bromide treatment of glucose-containing solids and chemical reactions using water-soluble carbodiimide technology, glutaraldehyde linking and the like.

In addition, U.S. Pat. No. 4,357,311 to Schutt discloses a method for preparing an activated microporous substrate to which an antibody can be covalently bonded through trichloro-triazine to yield an activated substrate. That method can also be used herein. Further, numerous methods for immobilizing enzymes that are applicable for affixing a receptor to a matrix are discussed in *Enzyme Technology*, published by Noyes Data Corporation (1983) at pages 38 to 59.

Solid phase supports designed for use in organic solvents are also useful for preparing immobilized catalyst molecules. These supports and the resulting immobilized catalyst molecules are "insoluble" in the organic solvent utilized for the reaction, as was discussed for the water-insoluble immobilized catalyst discussed hereinbefore.

The glass beads discussed before can be utilized as the solid phase support, as can cross-linked polystyrene beads as are utilized in solid phase peptide synthesis. Preferred cross-linked polystyrene beads for use in preparing immobilized catalyst molecules include a reactive halomethyl group, or a group such as aminomethyl or carboxymethyl that can react with a carboxyl or amine group, respectively, of the catalyst molecule to link the catalyst molecule to the solid phase support.

The before-discussed methods are carried out using an immobilized solid phase-bound catalyst in a manner similar to the manner utilized with a totally liquid composition as in an aqueous composition, an organic solvent composition or in a reverse micelle-containing composition, except that solid and liquid phases are present. Those solid and liquid phases are typically separated when the reaction product is recovered, with the reaction product typically being the liquid phase.

A catalytic method of this invention utilizes a liquid composition such as an aqueous medium as a portion of the reaction mixture that also includes the reactant diene and dienophile molecules and catalyst molecule. That aqueous medium typically contains water and buffer salts.

In addition, the medium can contain other salts such as sodium chloride, as well as water-soluble calcium and magnesium salts as are frequently found in protein-containing media. Other water-soluble polyvalent metal salts such as iron, zinc and cobalt salts can also be present and are useful complexing agents where the reactant ligand is comprised of two separate molecules. Organic solvents such as methanol, ethanol, acetonitrile, dimethyl sulfoxide, dioxane, hexamethylphosphoramide and N,N-dimethylforamide can also be present, as already noted. Surface active agents that emulsify the reactant ligand and receptor molecule can also be present. The critical feature of ingredients present in the composition of the reaction mixture is that those ingredients not substantially interfere with or inhibit the catalytic reaction as by denaturation of the receptor molecule.

An aqueous medium typically has a pH value of about 5 to about 9, and preferably about pH 6.0 to about 8.0. pH values greater and less than those recited values can also be utilized so long as the catalyzed reaction is again not substantially interfered with or inhibited.

The catalytic reactions are typically carried out at ambient room temperature; i.e., at about 20 to about 25 degrees C., and at an ambient atmospheric pressure where the composition is aqueous. However, temperatures down to about the freezing point of the aqueous medium and up to about the boiling point of the medium at atmospheric pressure can also be used. As is known, proteins such as the catalyst molecule tend to denature at elevated temperatures such as those at which an aqueous medium boils, e.b. at about 100 degrees C., and thus temperatures below about 40 degrees C. are preferred. As is also well known, reactions that follow multimolecular kinetic expressions decrease in rate as the temperature decreases. Thus, a minimal temperature of about 15 degrees is preferred. Reactions at greater than atmospheric pressure are also comtemplated.

The use of an organic solvent or reverse micelles rather than a substantially aqueous medium as discussed previously can aid in overcoming the denaturation problems associated with using a proteinaceous material such as a catalyst molecule described herein at elevated temperatures such as near 100 degrees C. In addition, used of such non-aqueous, substantially water-free organic solvent systems can enhance the solubility of the reactant diene and dienophile molecules at any useful temperature.

The reactants are present in a reaction mixture in an amount up to their solubility in the aqueous medium. A two phase system that includes insoluble reactant ligands can also be used, but normally is not so used. Normally used concentrations of the reactants are about 0.1 micromolar ($\mu$M) to about 10 millimolar (mM), with that amount also being a function of the solubility of the reactants in the composition of the reaction mixture. Where the product is desired, per se, relatively higher concentrations are used as compared to lower concentrations where a reaction mechanism or reaction kinetics are to be studied.

An effective amount of the catalyst molecule is also present. That effective amount is typically a catalystic amount; i.e., the catalyst molecule is used at a molar ratio to the reactants of about 1:2 to about 1:100,000, with a molar ration of about 1:10 to about 1:100 being preferred. The mole ratio of catalyst molecule to reactants typically depends upon the specific activity of the catalyst molecule toward the reactants, and the purpose of the user in running the reaction. Thus, where the product is desired, a relatively higher concentration of catalyst and higher catalyst to reactants ratio are used. Where the reaction mechanism or kinetics of the reaction are being studied, a lower concentration and ratio are typically used. A stoichiometric amount of catalyst molecule or more can also be used, but since the catalyst molecule is a catalytic molecule, use of even a stoichiometric amount can be wasteful. Thus, at least a catalytic amount of the catalyst molecule is utilized.

As noted earlier, the reaction mixture of reactants and catalyst molecules in the liquid composition is maintained for a time period sufficient for the cyclic reaction product to form. That maintenance time can vary widely depending on the purpose of carrying out the reaction, and other well known reaction parameters such as temperature and concentration.

For example, at a given temperature and concentration, maintenance times on the order of minutes can be used where reaction kinetics or mechanisms are studied, whereas maintenance times of hours and days can be utilized where the cyclic reaction product is desired to be recovered or otherwise used. Specific reaction maintenance times can be readily determined by a skilled worker to suit his or her particular desires.

VI. Preparation of Conjugates, Inocula and Monoclonal Antibodies

Antibodies are induced by immunization of a host animal such as a mouse, rat, rabbit, goat, or horse with a conjugate of the immunizing haptenic ligand linked to an immunogenic carrier molecule such as a protein. A wide variety of techniques are known and contemplated for linking a useful immunogenic hapten to an immunogenic carrier molecule. The exemplary immunogenic hapten utilized herein was linked to its carrier molecule keyhole limpet hemocyanin (KLH) by the reaction of an activated ester with free amino groups of the carrier protein.

In another exemplary situation, the immunizing hapten can contain a mercaptan group that is utilized for the linkage. Thus, conjugates of immunizing haptenic ligand molecules with carriers such as KLH can be prepared, for example, by activation of the carrier with a coupling agent such as MBS (m-maleimidobenzoyl-N-hydroxy succinimide ester), and coupling to the thiol group of the immunizing haptenic ligand. See, for example, Liu et al., Biochem., 80, 690 (1979). As is also well known in the art, it is often beneficial to bind a compound to its carrier by means of an intermediate, linking group.

Useful immunogenic carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the immunogen than upon the determinant portion of the immunogen, and is based upon criteria not particularly involved in the present invention. For example, if the conjugate is to be used in laboratory animals, a carrier that does not generate an untoward reaction in the particular animal should be selected.

More specifically, Compound 2 herein was prepared from 1,2,3,4,10,10-hexachloro-5-norbornene-2,3-dicarboxylic anhydride (Aldrich) and 6-aminocaproic acid. A Diels-Alder reaction between hexachlorocyclopentadiene and N-ethylmaleimide yielded Compound 3 that was used as an antigen ligand in inhibition studies. Each of the new compounds gave satisfactory spectroscopic data.

The N-hydroxysuccinimide ester of hapten Compound 2 was coupled to keyhole limpet hemocyanin, and the resulting protein conjugates were used to generate an immune response in 129 GIX+ mice. Standard protocols were used to fuse mouse spleen cells with SP2/0+ myeloma cells, as are discussed elsewhere herein. IgG antibodies specific for the hapten were isolated and purified as previously described [Hilvert et al. Proc. Natl. Acad. Sci. USA, 84:4953 (1988) and Hilvert et al., J. Am. Chem. Soc., 110:5593 (1988)].

Proteins were judged >95 percent pure by sodium dodecylsulfate polyacrylamide gel electrophoresis (SDS-PAGE) with Coomassie blue staining. Antibody concentration was determined from $A_{280}$ ($\epsilon^{0.1\%}$ 1.40 mL $mg^{-1}$ $cm^{-1}$) and a molecular weight of 160,000.

In a generalized antibody preparation, the carrier-hapten conjugate is dissolved or dispersed in an aqueous composition of a physiologically tolerable diluent such as normal saline, PBS, or sterile water to form an inoculum. An adjuvant such as complete or incomplete Freund's adjuvant (CFA or IFA) or alum can also be included in the inoculum. The inoculum is introduced as by injection into the host animal used to raise the antibodies in an amount sufficient to induce antibodies, as is well known. The animal is then maintained for a time period sufficient for the animal to produce cells secreting antibody molecules that immunoreact with the immunizing or antigenic hapten.

A suspension of antibody-producing (-secreting) cells removed from the immunized mammal is then prepared. This is typically accomplished by removing the spleen of the animal and mechanically separating the individual spleen cells in a physiologically tolerable medium using methods well known in the art.

The suspended antibody-producing cells are treated with a transforming agent capable of producing a transformed ("immortalized") cell line. Transforming agents and their use to produce immortalized cell lines are well known in the art and include DNA viruses such as Epstein Barr Virus (EBV), Simian Virus 40 (SV40), Polyoma Virus and the like, RNA viruses such as Moloney Murine Leukemia Virus (MoMuLV), Rous Sarcoma Virus and the like, myeloma cells as are discussed hereinafter, and the like.

In preferred embodiments, treatment with the transforming agent results in the production of a hybridoma by fusing the suspended spleen cells with mouse myeloma cells from a suitable cell line by the use of a suitable fusion promoter. The preferred ratio is about 5 spleen cells per myeloma cell. A total volume of about $10^8$ splenocytes.

The cell line used should preferably be of the so-called "drug resistant" type, so that unfused myeloma cells do not survive in a selective medium, whereas hybrids survive. The most common class is 8-azaguanine resistant cells lines, which lack the enzyme hypoxanthine guanine phophoribosyl transferase and cannot be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. Although the preferred fusion promoter is polyethylene glycol having an average molecule weight from about 1000 to about 4000 (commercially available as PEG 1000, etc.), other fusion promoters known in the art can be employed.

The transformed cells are then cloned, preferably to monoclonality. The cloning is preferably performed in a tissue culture medium that does not support non-transformed cells. When the transformed cells are hybridomas, this is typically performed by diluting and culturing in separate containers the mixture of unfused spleen cells, unfused myeloma cells, and fused cells (hybridomas) in a selective medium that does not support the unfused myeloma cells. The mixture is cultured for a time sufficient to permit death of the unfused cells (about one week). The dilution can be a type of limiting one, in which the volume of diluent is statistically calculated to isolate a certain number of cells (e.g., 1–4) in each separate container (e.g., each well of a microtiter plate). The medium is one (e.g., HAT medium) that does not support the drug-resistant (e.g., 8-azaguanine resistant) unfused myeloma cell line.

The tissue culture medium of the cloned transformants is evaluated for the presence of secreted anti-hapten antibody molecules using well known immunological techniques such as the ELISA technique described hereinafter.

Once a desired transformant has been identified, it is selected and grown in a suitable tissue culture medium for a suitable length of time, followed by recovery of the desired antibody from the culture supernatant. The suitable medium and suitable length of culturing time are known or are readily determined.

To produce a much greater concentration of slightly less pure monoclonal antibody, the desired mouse hybridoma, for example, can be injected into mice, preferably syngeneic or semisyngenic mice. The hybridoma causes formation of antibody-secreting tumors after a suitable incubation time that result in a high concentration of the desired antibody (about 0.5-20 mg/ml) in the bloodstream and peritoneal exudate (ascites) of the host mouse.

Media useful for the preparation of these compositions are both well known in the art and commercially available and include synthetic culture media, inbred mice and the like. An exemplary synthetic medium is Dulbecco's minimal essential medium [DMEM; Dulbecco et al., *Virol.*, 8:396 (1959)] supplemented with 4.5 gm/1 glucose, 20 mm glutamine, and 20 percent fetal calf serum. An exemplary inbred mouse strain is the Balb/c.

It is preferred that the myeloma cell line be from the same species as the antibody-secreting cells. Therefore, fused hybrids such as mouse-mouse hybrids Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/O-Ag14 (ATCC CRL 1581), P3X63 Ag8U.1 (ATCC CRL 1597), Y3-Agl.2.3. (deposited at Collection Nationale de Cultures de Microorganisms, Paris, France, number I-078) and P3X63Ag8 (ATCC TIB 9). The non-secreting murine myeloma line Sp2/O+ or Sp2/O-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used herein for generation of the ascites fluid were (BALB/c ×129GIX+) $F_1$ mice bred in the mouse colony of the Scripps Clinic and Research Foundation, La Jolla, Calif., however, when animals other than mice are used for preparation of the hybridomas, mice or that animal type can be used for the production of ascites fluid.

In particular, an exemplary monoclonal receptor was produced by the standard hybridoma technology of Kohler et al., *Nature*, 256, 495 (1975). Specifically, female 129GIX+mice were immunized by intraperitoneal injection with an inoculum of 100 micrograms of conjugate (e.g., Compound 2 bound to KLH) in 300 microliters of a 1:1 mixture of phosphate buffered saline (PBS) pH 7.4 and complete Freund's adjuvant. Two weeks later, the mice were again injected in a like manner with 50 micrograms of the foregoing conjugate in 300 microliters of a 1:1 mixture of PBS (pH 7.4) and 10 mg/ml alum. After an additional eight weeks, the mice were immunized intravenously with 50 micrograms of the conjugate in 200 microliters of PBS (pH 7.4).

Serum titers were determined using a BSA conjugate of Compound 2 as antigen in an ELISA. Mice with a serum titer (the dilution at which 50 percent of the available ligand is bound to antibody) of 1:6400 were sacrificed. The spleens were removed from the mice and the spleen cells were fused to myeloma cells.

The spleens cells were pooled and a single cell suspension was made. Nucleated spleen cells $(1.4\times10^8)$ were then fused with $3\times10^7$ Sp2/O non-secreting myeloma cells in the presence of a cell fusion promoter (polyethylene glycol 2000). The hybridoma that produces a particular monoclonal antibody was selected by seeding the spleen cells in 96-well plates and by growth in Dulbecco's modified Eagle medium (DMEM) containing 4500 mg/liter glucose (10 percent), 10 percent fetal calf serum (FCS), hypoxanthine, aminopterin and thymidine (i.e., HAT medium) which does not support growth of the unfused myeloma cells.

After two to three weeks, the supernatant above the cell clone in each well was sampled and tested by an ELISA assay (enzyme linked immunosorbent assay as described hereafter) for the presence of antibodies that bound to a conjugate of Compound 2-linked to bovine serum albumin (BSA). Positive wells were cloned twice by limiting dilution. Those clones that continued to produce Compound 2-specific antibody after two clonings were expanded to produce larger volumes of supernatant fluid.

A total of twenty-four monoclonal antibodies and their corresponding hybridomas were identified using the above preparation and screening techniques. Five of those hybridomas were selected for initial studies and were grown in mice as discussed herein, with the remaining nineteen hybridomas being frozen and stored for future studies. Ascites from the five hybridomas were purified to yield the useful monoclonal antibody combining site-containing molecules as discussed hereinafter.

Two monoclonal antibodies from those initially studied five monoclonals catalyzed the Diels-Alder [4+2] cycloaddition/fragmentation reaction of tetrachlorothiophene dioxide and N-ethylmaleimide; i.e., the reaction rate in the presence of a monoclonal antibody catalyst was greater than the background uncatalyzed rate. Of those two, one hybridoma and its monoclonal antibodies, both designated 1E9, were studied further. Further studies are being carried out with the remaining four monoclonal antibodies.

Monoclonal antibody catalytic molecules utilized herein were precipitated from the ascitic fluids with ammonium sulfate, purified further by affinity chromatography on protein A or protein G, and then purified by FPLC ion-exclusive chromatograph on a Pharmacia Mono Q HR 10/10 column. Such purified monoclonal antibodies were judged to be more than 95 percent pure monoclonal antibody by SDS-PAGE using Coomassie blue staining.

Hybridoma 1E9 was received at the American Type Culture Collection, 12301 Parklawn Drive, Rockville, Md. on Oct. 12, 1989, and was given the accession number HB 10261. The present deposit was made in compliance with the Budapest Treaty requirements that the duration of the deposits should be for 30 years from the date of deposit or for 5 years after the last request for the deposit at the depository or for the enforceable life of a U.S. patent that matures from this application, whichever is longer. The hybridomas will be replenished should they become non-viable at the depository.

VII. Enzyme-linked Immunosorbent Assay (ELISA)

The binding to haptenic ligands was assayed by ELISA with antibody at fixed concentration in the range of its titer and varying reagent or ligand concentration. Assays were performed in flat-bottom 96-well microtiter plates (Costar 3690).

Illustratively, the wells were coated with a solution comprising Compound 2 linked to BSA as the antigen ligand in phosphate-buffered saline (PBS) using 25 microliters of solution per well. Antigen ligands were used at a 1:500 dilution of 25 mg/ml stock solution. The plates were then incubated overnight (about 18 hours) at 37 degrees C. in a warm room, or for 1-2 hours in a drying oven. The dried plates were stored at 4 degrees C. until use.

The wells were fixed prior to use with 50 $\mu$l of methanol per wall for 5 minutes at room temperature, followed by discarding of the methanol and drying for 5-10 minutes. This step can also be omitted if desired.

To each well were thereafter added 50 $\mu$l of 3 weight percent BSA in PBS, with the solutions being incubated for 1-4 hours at 37 degrees C. in a moist chamber. The BSA solutions were thereafter shaken out, but not dried.

An antibody-containing solution (25 $\mu$l/well) diluted in 1 weight percent BSA was added to each well and incubated overnight (about 18 hours) at 25 degrees C. in a moist chamber. The volume ratio of antibody-containing composition to the diluting BSA solution was dependent upon the source of the antibody-containing solution as follows: hybridoma supernatant 1:1; mouse serum 1:100; and ascites 1:1000.

The liquid was then removed from the wells, and each well was washed ten times with deionized water, with any excess water being shaken out after the last rinse. A solution containing glucose oxidase-linked goat-anti-mouse antibodies diluted 1:1000 in 1 percent BSA/PBS was added at 25 $\mu$l/well to each well. The resulting admixtures were then incubated for 1-2 hours at 37 degrees C. in a moist chamber.

The plates were again washed ten times with deionized water, with excess water being shaken out of the wells. Developing reagent (below; 50 $\mu$l/well) was then admixed into the wells, and the plates were covered with parafilm while the green color developed. The plates were read in a multiscan plate reader at 414 nm 30 to 60 minutes after admixture of the developing reagent.

The developing reagent solution contained the following materials: 25 $\mu$l of 0.1 M phosphate buffer (pH 6.0); 3 ml of 20 percent glucose in water (used after mutarotation, and stored at 4 degrees C. after filter sterilizing); 200 $\mu$l of 0.1 percent horseradish peroxidase in 0.1 M phosphate buffer; 200 $\mu$l of freshly prepared ABTS dye [45 mg/ml of phosphate buffer; "2,2'-azinodi[3-athylbenzthiazolinsulfonat(6)] deammonium salt, kryst", Boehringer Mannheim, cat. #102946].

VIII. Results

The transition state for a Diels-Alder cycloaddition is highly ordered resembling product more closely than starting material [Brown et al., Tet. Lett., 25:4609 (1984)]. However, the product of that reaction is not an appropriate hapten for generating catalyst antibodies, since severe product inhibition would be expected to prevent efficient turnover of the catalyst.

An alternate strategy is shown in FIG. 1. Tetrachlorothiophene dioxide (TCTD) reacts with maleimides in Diels-Alder [4+2] cycloaddition reactions to give an unstable, bicyclic reactive intermediate Compound 1 that subsequently extrudes $SO_2$ in a fragmentation reaction to give tetrachlorodihydrophthalimide as the cyclic reaction product [Raasch, J. Org. Chem., 45:856 (1980)].

It was reasoned that a stable analog of the bicyclic adduct (reactive intermediate) could elicit an antibody combining site with the proper shape for promoting the target reaction. As the final reaction product does not closely resemble the transition state for the first Diels-Alder reaction, product inhibition is minimized and multiple turnovers of the catalyst can occur.

Five of the twenty-four high-affinity monoclonal antibodies against immunizing hapten Compound 2, a stable analog that is isologous to the bicyclic reaction intermediate Compound 1 were prepared, as noted before. One of the catalytic monoclonal antibody molecules, denominated 1E9, was studied in detail.

Because TCTD reacts with lysine residues on the surface of the immunoglobulins, it was necessary to reduce the nucleophilicity of the amino groups by exhaustive reductive methylation [Jentoft et al., J. Biol. Chem., 254:4359 (1979)]. TCTD was shown to be stable in the presence of the methylated antibodies, which also retained high affinity for the hapten as judged by ELISA [Butler, Enzyme-Immunoassay, Maggio, E.T. ed., CRC Press, Boca Raton, FL, page 41 (1980)]]. Chemical modification of immunoglobulins in this way is likely to be of general value, as it will permit reactive molecules like epoxides, Michael acceptors or other alkylating agents to be employed as substrates for catalytic antibodies.

The methylated antibodies were assayed at 25 degrees C. for their ability to promote the Diels-Alder [4+2] cycloaddition/fragmentation reaction between TCTD and N-ethylmaleimide (NEM) in aqueous buffer (20 mM MES, 100 mM NaCl, pH 6.0) containing 10 percent acetonitrile. Cycloadditions were followed by monitoring the disappearance of TCTD at 330 nm or by analytical reverse-phase HPLC. HPLC kinetic assays were performed on a Vydac C-18 218-TP-510 reverse phase column (10 mm×25 cm, 2 mL/min, gradient elution from 100 percent $H_2O$ to 60:40 $CH_3CN:H_2O$ in 20 minutes, then 5 minutes at the latter solvent composition) using acetophenone as an internal standard.

The products of the reaction, dihydro(N-ethyl)tetrachlorophthalimide and the fully oxidized (N-ethyl)tetrachlorophthalimide, a commercially sold chemical, were isolated and characterized. Sulfur dioxide expulsion was detected independently by following its bleaching of malachite green at 617 nm.

Multiple turnovers of catalytic antibody 1E9 (>50) were observed in the assay reaction without diminution of the catalytic activity. Several lines of evidence demonstrate that the observed catalysis is not artefactual. The antibody-promoted process is first order with respect to immunoglobulin concentration, and its specificity matches expectations based on hapten structure. Thus, N-ethylmaleimide is a good substrate for the catalyst, but maleimide is not. Also the catalyzed reaction is specifically inhibited by the antigenic hapten Compound 3, a close analog of the hapten used for immunization. Preincubation of the antibody with an equimolar amount of Compound 3 stopped the oatalyzed reaction completely.

When initial rates with the antibody catalyst were measured as a function of NEM concentration, holding the concentration of TCTD constant, saturation kinetics were observed At 0.61 mM TCTD, for example, the apparent values of $k_{cat}$ and $(K_m)_{NEM}$ were $4.3 \pm 0.3$ min$^{-1}$ and $21 \pm 4$ mM, respectively.

The low solubility of TCTD in the composition of the aqueous reaction mixture prevented determination of its $K_m$ value and, hence, the true $K_{cat}$ for the reaction. However, comparison of $(k_{cat})_{app}$ obtained at 0.61 mM TCTD with the second-order rate constant for the uncatalyzed cycloaddition ($0.040 \pm 0.007$ M$^{-1}$ min$^{-1}$) yields an apparent effective molarity of 110 M per binding site. Because $(k_{cat})_{app}$ is linearly dependent on TCTD concentration in this range, the true effective molarity must be substantially higher than this value.

Whereas maleimide itself did not undergo the catalyzed reaction, N-methylmaleimide reacted, as did the N-ethyl, N-propyl and N-butyl isomers. The N-ethyl isomer, discussed above, reacted more rapidly than did the N-methyl isomer, and preliminary results indicate that both the N-propyl and N-butyl isomers reacted about twice as rapidly as did the N-ethyl compound. Thus, as the substituent alkyl group of the reactant dienophile molecule was lengthened through homologous methylene group additions, the catalyzed reaction rate appeared to increase and then level off as the size of the substituent approached the size of the substituent linking group of the immunogenic haptenic linking group.

These studies provide the first example of an antibody-catalyzed Diels-Alder [4+2] cycloaddition/fragmentation reaction and demonstrate the feasibility of using catalytic antibody technology to promote important non-physiological reactions. They are particularly notable with regard to 1) the design of the hapten so as to minimize product inhibition and 2) the use of chemically modified antibodies to permit study of reactive substrate molecules.

The foregoing is intended as illustrative of the present invention but not limiting. Numerous variations and modifications may be effected without departing from the true spirit and scope of the novel concepts of the invention.

What is claimed is:

1. A catalyst molecule comprising an antibody combining site that catalyzes the reaction of a dienophile molecule containing a reactive multiple bond and a conjugated cyclic diene molecule to form a cyclic reaction product from a Diels-Alder [4+2] cycloaddition/fragmentation reaction in which said dienophile molecule and cyclic diene molecule form a reactive intermediate upon cycloaddition and prior to fragmentation, said cyclic conjugated diene molecule having a structure that includes a fugitive leaving group within a five- or six-membered ring, said fugitive leaving group being substantially stable when present in said cyclic conjugated diene and being expelled from said reactive intermediate as a molecular entity to form said cyclic reaction product, said catalyst molecule immunoreacting with an antigent that is an analog to a transition state leading to the formation of the reactive intermediate, said antigen being isologous to the reactive intermediate and having a structure that (i) includes a [2.2.1] or [2.2.2] bicyclic ring system absent from the reaction product, (ii) contains at least one endocyclic double bond fewer in said bicyclic ring system than the number of endocyclic double bonds present in the reaction product, and (iii) contains a group or moiety that is isostructural to the fugitive leaving group and is substantially less reactive in the antigen than is the fugitive leaving group in the reactive intermediate.

2. The catalyst molecule according to claim 1 wherein said catalyst molecule is an intact antibody molecule.

3. The catalyst molecule according to claim 1 wherein said dienophile molecule has a cyclic structure.

4. The catalyst molecule according to claim 1 wherein said fugitive leaving group forms a gaseous compound upon the formation of the reaction product.

5. The catalyst molecule according to claim 1 wherein said dienophile includes an electron withdrawing substituent moiety relative to hydrogen that is located alpha to said reactive multiple bond.

6. A catalyst molecule comprising an antibody combining site that catalyzes the reaction of a cyclic dienophile molecule with a cyclic diene molecule to form a Diels-Alder [4+2] cycloaddition/fragmentation cyclic reaction product that contains a five- or six-membered ring formed by said reaction and that includes at least two endocyclic conjugated double bonds, said dienophile molecule and cyclic diene molecule forming a reactive intermediate upon cycloaddition and prior to fragmentation, said dienophile molecule containing a reactive multiple bond and including a moiety that is electron-withdrawing relative to hydrogen located at a position alpha to said reactive multiple bond, said conjugate diene molecule having a structure that includes a five- or six-membered ring having a fugitive leaving group that is substantially stable when present in said cyclic conjugated diene and forms a gaseous compound in forming said cyclic reaction product, said catalyst molecule immunoreacting with an antigen that is an analog to a transition state leading to the formation of the reactive intermediate, said antigen being isologous to the reactive intermediate and having a structure that (i) includes a [2.2.1] or [2.2.2] bicyclic ring system absent from the reaction product (ii) contains at least one endocyclic double bond fewer in said bicyclic ring system than the number of endocyclic double bonds present in the reaction product, and (iii) contains a group or moiety that is isostructural to the fugitive leaving group and is substantially less reactive in the antigen than is the fugitive leaving group in the reactive intermediate.

7. The catalyst molecule according to claim 6 that is an intact antibody.

8. The catalyst molecule according to claim 6 wherein said antigen has a structure that corresponds to the formula

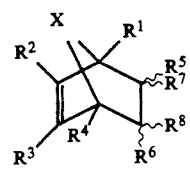

wherein X is isologous to said fugitive leaving group, $R^7$ and $R^8$ each contain a total of 1 to about 50 atoms, and each is selected from the group consisting of hydrogen, an electron-withdrawing group relative to hydrogen, and an electron-donating group relative to hydrogen, or $R^7$ and $R^8$ together form a ring containing up to eight atoms, and $R^1$, $R^2$, $R^3$, $R^4$, $R^5$ and $R^6$ are independently selected from the group consisting of hydrogen, halogen, $C_1$-$C_6$ lower alkyl, substituted $C_1$-$C_6$ lower alkyl, phenyl, substituted phenyl, benzyl, substituted benzyl, $C_1$-$C_6$ lower alkenyl, and $C_1$-$C_6$ substituted lower alkenyl, or $R^5$ and $R^6$ are absent and replaced by a double bond.

9. The catalyst molecule according to claim 8 wherein $R^1$, $R^2$, $R^3$ and $R^4$ are chloro, $R^5$ and $R^6$ are hydrogen, $R^7$ and $R^8$ together form a ring containing five atoms, and X is a —$CCl_2$— group.

10. The catalyst molecule according to claim 8 wherein primary amine groups present in said catalyst are protected from reaction with the diene, dienophile or the reaction product.

11. The catalyst molecule according to claim 8 wherein said catalyst molecule is secreted by hybridome 1E9 having the ATCC accession number HB 10261.

12. A method of forming a cyclic reaction product having a five- or six-membered ring that includes at least two endocyclic conjugated double bonds in a Diels-Alder [4+2] cycloaddition/fragmentation reaction that proceeds though a reactive intermediate comprising the steps of:

(a) admixing a dienophile molecule having a reactive multiple bond and cyclic conjugated diene molecule having a structure that includes a fugitive leaving group within a five- or six-membered ring with a catalyst molecule in a liquid composition to form a reaction mixture, said fugitive leaving group being substantially stable when present in said cyclic conjugated diene and being expelled from said reactive intermediate as a molecular entity to form said cyclic reaction product, said catalyst molecule comprising a monoclonal antibody combining site-containing molecule that catalyzes said reaction and immunoreacts with an antigen that is an analog to a transition state leading to the formation of the reactive intermediate, said antigen being isologous to the reactive intermediate and having a structure that (i) includes a [2.2.1] or [2.2.2] bicyclic ring system absent from the reaction product, (ii) contains at least one endocyclic double bond per molecule fewer in said bicyclic ring system than the number of endocyclic double bonds present in the reaction product, and (iii) contains a group or moiety that is isostructural to the fugitive leaving group and is substantially less reactive in the antigen than is the fugitive leaving group in the reactive intermediate; and (b) maintaining said reaction mixture for a time period sufficient for the reaction product to form.

13. The method according to claim 12 including the further step of recovering the reaction product.

14. The method according to claim 12 wherein said catalyst molecule is an intact antibody molecule.

15. The method according to claim 12 wherein said dienophile has a cyclic structure.

16. The method according to claim 12 wherein said cyclic reaction product is a cyclohexadiene derivative, and including the further step of oxidizing cyclohexadiene derivative reaction product to a benzene derivative.

17. A method of forming a cyclic reaction product that contains a five- or six-membered ring having at least two conjugated endocyclic double bonds in a Diels-Alder [4+2] cycloaddition/fragmentation reaction that proceeds through a reactive intermediate comprising the steps of:

(a) admixing a cyclic dienophile molecule and a cyclic conjugated diene molecule with a catalyst molecule in an aqueous liquid composition to form a reaction mixture, said cyclic dienophile molecule including a double bond that reacts with the two double bonds of said cyclic conjugated diene, said cyclic conjugated diene including a fugitive leaving group in a five- or six-membered ring, said fugitive leaving group being substantially stable when present in said cyclic conjugated diene and being expelled from said reactive intermediate as a molecular entity to form said cyclic reaction product, said catalyst molecule catalyzing the formation of said cyclic reaction product from said cyclic dienophile and said cyclic conjugated diene and comprising a monoclonal antibody combining site-containing molecule that immunoreacts with an antigen that is an analog to a transition state leading to the formation of the reactive intermediate, said antigen being isologous to the reactive intermediate and having a structure that (i) includes a [2.2.1] or [2.2.2] bicyclic ring system absent from the reaction product, (ii) contains at least one endocyclic double bond per molecule fewer in said bicyclic ring system than the number of endocyclic double bonds present in the reaction product, and (iii) contains a group or moiety that is isostructural to the fugitive leaving group and is substantially less reactive in the antigen than is the fugitive leaving group in the reactive intermediate; and (b) maintaining said reaction mixture under biological conditions for a time period sufficient for the reaction product to form.

18. The method according to claim 17 including the further step of isolating said cyclic reaction product.

19. The method according to claim 18 wherein said cyclic reaction product is a cyclohexadiene derivative, and said reaction mixture is maintained under aerphic conditions.

20. A method of preparing a monoclonal antibody combining site-containing molecule capable of catalyzing the formation of a reaction product containing a five- or six-membered ring and at least two endocyclic double bonds in a Diels-Alder [4+2] cycloaddition/fragmentation reaction that proceeds through a reactive intermediate comprising the steps of:

(a) immunizing an animal host with an immunogen that is relatively non-reactive in the catalyzed reaction, said immunogen having a structure that is isologous to the structure of a transition state leading to formation of a Diels-Alder [4+2] cycloadditon reactive intermediate product formed by reaction of a dienophile molecule containing a reactive multiple bond and a cyclic conjugated diene having a fugitive leaving group in a five- or six-membered ring, and which cycloaddition intermediate product is a reactive intermediate in the formation of said reaction product, said fugitive leaving group being substantially stable when present in said cyclic conjugated diene and being expelled from said reactive intermediate as a molecular entity in forming said cyclic reaction product, said immunogen having a structure that (i) includes a [2.2.1] or [2.2.2] bicyclic ring structure absent from the reaction product, (ii) contains at least one endocyclic double bond per molecule fewer in said bicyclic ring system than the number of endocyclic double bonds present in the reaction product, and (iii) contains a group or moiety that is isostructural to the fugitive leaving group and is substantially less reactive in the immunogen than is the fugitive leaving group in the reactive intermediate;

(b) forming hybridoma cells with antibody-secreting cells from an immunized animal host that secretes antibodies that immunoreact with said immunogen; and (c) clonging and culturing the hybridoma cells that secrete monoclonal antibodies that immunoreact with said immunogen.

21. The method according to claim 20 including the further step of recovering said monoclonal antibodies.

22. The method according to claim 21 including the further step of reacting amino groups present in said recovered monoclonal antibodies with protective groups that do not substantially inhibit the reaction catalyzed by said monoclonal antibodies.

23. A catalyst molecule comprising an antibody combining site that catalyzes reaction of a dienophile molecule containing a reactive double bond and a halogenated thiophene 1,1-dioxide as diene to form a bicyclic reaction product in a Diels-Alder [4+2] cycloaddition/fragmentation reaction that proceeds through a reactive intermediate having a [2.2.1] bicyclic ring system that includes an $SO_2$ group that is expelled in forming said bicyclic reaction product, said catalyst molecule immunoreacting with an antigen that is an analog to the transition state for formation of the reactive intermediate, is isologous to said reactive intermediate and having a structure that (i) includes a [2.2.1] bicyclic ring system absent from the reaction product, (ii) contains one endocyclic double bond fewer in said [2.2.1] bicyclic ring system than the number of endocyclic double bonds present in the reaction product, and (iii) contains a $CCl_2$ group in the position occupied by said $SO_2$ group of the reactive intermediate.

24. The catalyst molecule according to claim 23 wherein said dienophile is an $N-C_1-C_4$ alkyl maleimide.

25. The catalyst molecule according to claim 23 that is secreted by hybridome 1E9 having the ATCC accession number HB 10261.

26. A method of forming a bicyclic reaction product having a six-membered ring that includes two endocyclic conjugated double bonds in a Diels-Alder [4+2] cycloaddition/fragmentation reaction that proceeds through a reactive intermediate having [2.2.1] bicyclic ring that includes an $SO_2$ group that is expelled in forming the bicyclic reaction product comprising the steps of:

(a) admixing a dienophile molecule containing a reactive double bond and a halogenated thiophene 1,1-dioxide as diene with a catalyst molecule in a liquid composition to form a reaction mixture, said catalyst molecule comprising a monoclonal antibody combining site-containing molecule that catalyzes said reaction and immunoreacts with an antigen that is an analog to a transition state for formation of the reactive intermediate, is isologous to the reactive intermediate, and has a structure that (i) includes a [2.2.1] bicyclic ring system absent from the reaction product, (ii) contains one endocyclic double bond fewer in said [2.2.1] bicyclic ring system than the number of endocyclic double bonds present in the reaction product, and (iii) contains a $CCl_2$ group in the position occupied by said $SO_2$ group of the reactive intermediate; and (b) maintaining said reaction mixture for a time period sufficient for the reaction product to form.

27. The method according to claim 26 wherein said dienophile is an $N-C_1-C_4$ alkyl maleimide.

28. The method according to claim 26 wherein said catalyst molecule is an intact antibody molecule.

29. The method according to claim 28 wherein said catalyst molecule is secreted by hybridoma 1E9 having the ATCC accession number HB 10261.

* * * * *

UNITED STATES PATENT AND TRADEMARK OFFICE
CERTIFICATE OF CORRECTION

PATENT NO.    : 5,208,152
DATED         : May 4, 1993
INVENTOR(S)   : Donald Hilvert et al.

It is certified that error appears in the above-identified patent and that said Letters Patent is hereby corrected as shown below:

Column 1, after the heading "DESCRIPTION" and before the heading "1. Technical Field", insert the following paragraph:

--This invention was made with government support under Contract No. GM 38273 awarded by the National Institutes of Health. The government has certain rights in the invention.--

Signed and Sealed this

First Day of March, 1994

BRUCE LEHMAN

Attest:

Attesting Officer

Commissioner of Patents and Trademarks